(12) United States Patent
Watanabe

(10) Patent No.: US 12,256,516 B2
(45) Date of Patent: Mar. 18, 2025

(54) COOLING DEVICE OF ENDOSCOPE

(71) Applicant: OLYMPUS CORPORATION, Tokyo (JP)

(72) Inventor: Masaaki Watanabe, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 441 days.

(21) Appl. No.: 17/869,090

(22) Filed: Jul. 20, 2022

(65) Prior Publication Data
US 2022/0354355 A1 Nov. 10, 2022

Related U.S. Application Data

(63) Continuation of application No. PCT/JP2020/003246, filed on Jan. 29, 2020.

(51) Int. Cl.
*H05K 7/20* (2006.01)
*A61B 1/05* (2006.01)
(Continued)

(52) U.S. Cl.
CPC .......... *H05K 7/20145* (2013.01); *A61B 1/05* (2013.01); *A61B 1/128* (2013.01);
(Continued)

(58) Field of Classification Search
CPC .. H05K 7/20145; H05K 7/20209; A61B 1/05; A61B 1/128; A61B 1/12; G02B 23/2476; G02B 23/2484
(Continued)

(56) References Cited

U.S. PATENT DOCUMENTS 5,361,188 A 11/1994 Kondou et al.
6,185,481 B1 2/2001 Kondou et al.
(Continued)

FOREIGN PATENT DOCUMENTS

JP 04-162497 A 6/1992
JP H10-163660 A 6/1998
(Continued)

OTHER PUBLICATIONS

Kondo Yoshihiro; Ohashi Shigeo; Nakajima Tadakatsu; Miyazaki Masayoshi; Fuse Shohei; Ishii Takayoshi; Amano Osamu; Mino Yoshihiro, "Apparatus for Cooling Electronic Apparatus", Hitachi Ltd, Entire Document (Translation of JP H11135694) (of record, cited in the IDS, including Original Document). (Year: 1999).*
(Continued)

*Primary Examiner* — Stephen S Sul
(74) *Attorney, Agent, or Firm* — Scully, Scott, Murphy & Presser, P.C.

(57) ABSTRACT

Provided is a cooling device of an endoscope device. The cooling device includes: a box; a first communicating hole that is a hole provided in the box; a second communicating hole that is a hole provided in the box; a second fan that is provided at the second communicating hole, the second fan being configured to guide gas to an exterior of the box through the second communicating hole to generate an airflow in the box, the gas having introduced into the box from the first communicating hole; and a duct configured to house a heat generator to be cooled, the duct being positioned in the box to allow the airflow to pass through an inside of the duct.

11 Claims, 18 Drawing Sheets

(51) Int. Cl.
 *A61B 1/06* (2006.01)
 *A61B 1/12* (2006.01)
 *G02B 23/24* (2006.01)
(52) U.S. Cl.
 CPC ..... *G02B 23/2476* (2013.01); *G02B 23/2484* (2013.01); *H05K 7/20209* (2013.01)
(58) Field of Classification Search
 USPC .................................................. 361/679.49
 See application file for complete search history.

(56) References Cited

U.S. PATENT DOCUMENTS

| | | | | |
|---|---|---|---|---|
| 6,452,797 | B1* | 9/2002 | Konstad | H01L 23/467 |
| | | | | 257/E23.099 |
| 6,462,948 | B1* | 10/2002 | Leija | H05K 7/20727 |
| | | | | 174/16.3 |
| 6,678,157 | B1* | 1/2004 | Bestwick | H05K 7/20163 |
| | | | | 165/104.34 |
| 6,785,145 | B1* | 8/2004 | Wong | G06F 1/20 |
| | | | | 361/752 |
| 7,920,381 | B2* | 4/2011 | Kitahara | A61B 8/546 |
| | | | | 361/679.48 |
| 2002/0172008 | A1* | 11/2002 | Michael | H01L 23/467 |
| | | | | 361/720 |
| 2003/0214785 | A1 | 11/2003 | Perazzo | |
| 2004/0165349 | A1* | 8/2004 | Arbogast | H01L 23/467 |
| | | | | 257/E23.099 |
| 2005/0041392 | A1* | 2/2005 | Chen | H05K 7/20727 |
| | | | | 361/695 |
| 2005/0259393 | A1* | 11/2005 | Vinson | G06F 1/20 |
| | | | | 165/80.3 |
| 2011/0292580 | A1* | 12/2011 | Sun | G06F 1/20 |
| | | | | 361/679.5 |
| 2012/0050991 | A1* | 3/2012 | Tamanuki | H01L 23/467 |
| | | | | 361/697 |
| 2012/0127664 | A1* | 5/2012 | Shu | G06F 1/20 |
| | | | | 361/695 |
| 2012/0327589 | A1* | 12/2012 | Sun | G06F 1/181 |
| | | | | 361/679.47 |
| 2016/0192538 | A1* | 6/2016 | Yang | H05K 7/20145 |
| | | | | 361/692 |
| 2018/0174731 | A1* | 6/2018 | Fukuchi | H01F 27/08 |
| 2018/0317759 | A1 | 11/2018 | Watanabe et al. | |
| 2020/0008317 | A1* | 1/2020 | Pedoeem | H05K 7/20545 |
| 2020/0084911 | A1* | 3/2020 | Mitsui | H05K 7/20145 |
| 2022/0030742 | A1* | 1/2022 | Rehak | H05K 7/20154 |

FOREIGN PATENT DOCUMENTS

| | | |
|---|---|---|
| JP | H11-135694 A | 5/1999 |
| JP | H11-186767 A | 7/1999 |
| JP | 2008-263078 A | 10/2008 |
| JP | 6246451 B1 | 12/2017 |
| WO | 2016/143164 A1 | 9/2016 |
| WO | WO-2018084016 A1 * | 5/2018 ......... H01L 23/3672 |

OTHER PUBLICATIONS

Yaguchi, Yuichiro; Nakajima, Yuji; Ota, Takeshi, "Electronic Apparatus", May 11, 2018, Kabushiki Kaisha Toshiba; Toshiba Infrastructure Systems & Solutions Corporation, Entire Document (Translation of WO 2018084016). (Year: 2018).*

International Search Report dated Apr. 7, 2020 received in PCT/JP2020/003246.

\* cited by examiner

COOLING DEVICE OF ENDOSCOPE

CROSS-REFERENCE TO RELATED APPLICATION

This application is a continuation of International Application No. PCT/JP2020/003246, filed on Jan. 29, 2020, the entire contents of which are incorporated herein by reference.

BACKGROUND

1. Technical Field

The present disclosure relates to a cooling device of an endoscope.

2. Related Art

Endoscope systems for in-vivo observation of subjects have been used in the medical field. Typically, an elongated flexible insertion unit is inserted into a subject, such as a patient, and the interior of the subject is illuminated with illumination light from a distal end of this insertion unit (see, for example, Japanese Patent No. 6246451). The endoscope has a built-in light source and is connected to a processing device that controls the endoscope, for example. A suction hole, through which air is suctioned from the exterior, and a release hole, through which the air is released to the exterior, are formed in the processing device, and the air inside a housing (box) of the processing device is circulated by a fan being driven for ventilation in the housing.

SUMMARY

In some embodiments, provided is a cooling device of an endoscope device. The cooling device includes: a box; a first communicating hole that is a hole provided in the box; a second communicating hole that is a hole provided in the box; a second fan that is provided at the second communicating hole, the second fan being configured to guide gas to an exterior of the box through the second communicating hole to generate an airflow in the box, the gas having introduced into the box from the first communicating hole; and a duct configured to house a heat generator to be cooled, the duct being positioned in the box to allow the airflow to pass through an inside of the duct. The duct includes a first opening positioned upstream of the heat generator, a first fan that is provided at the first opening, the first fan being configured to guide the airflow into the duct to cause the airflow to come into contact with the heat generator, a second opening that is positioned downstream from the heat generator, the second opening being configured to guide the airflow taken in by the first fan to an exterior of the duct, a third opening that is provided downstream from the first opening and upstream of the second opening and that is open on a surface that is along a surface where the first opening is open, and a wall that includes an elevated portion on a periphery of the third opening to adjust the airflow, the elevated portion making a downstream side of the periphery higher than an upstream side of the periphery to allow the gas to flow into the duct from the third opening upon stoppage of the first fan.

In some embodiments, an endoscope processing device includes the cooling device of the endoscope device.

In some embodiments, provided is a cooling device of an endoscope device. The cooling device includes: a box; a first communicating portion that is a hole provided in the box; a second communicating portion that is a hole provided in the box; a second fan that is provided at the second communicating portion, the second fan being configured to guide gas to an exterior of the box through the second communicating portion to generate an airflow in the box, the gas having introduced into the box from the first communicating portion; and a duct configured to house a heat generator to be cooled, the duct being positioned in the box to allow the airflow to pass through an inside of the duct. The duct includes a first opening positioned upstream of the heat generator, a first fan that is provided at the first opening, the first fan being configured to guide the airflow into the duct to cause the airflow to come into contact with the heat generator, a second opening that is positioned downstream from the heat generator, the second opening being configured to guide the airflow taken in by the first fan to an exterior of the duct, a third opening that is provided downstream from the first opening and upstream of the second opening and that is open on a surface that is along a surface where the first opening is open, and a wall that includes an elevated portion on a periphery of the third opening to adjust the airflow, the elevated portion making a downstream side of the periphery higher than an upstream side of the periphery to allow the gas to flow into the duct from the third opening upon stoppage of the first fan.

The above and other features, advantages and technical and industrial significance of this disclosure will be better understood by reading the following detailed description of presently preferred embodiments of the disclosure, when considered in connection with the accompanying drawings.

DETAILED DESCRIPTION

Modes for implementing the disclosure (hereinafter, referred to as "embodiments") will be described hereinafter. Embodiments, which are medical endoscope systems for capturing and displaying in-vivo images of subjects, such as patients, will be described as examples of a system including a cooling device of an endoscope according to the disclosure. The disclosure is not limited by these embodiments. Description will be made by assignment of the same reference sign to portions that are the same, throughout the drawings.

First Embodiment

Figure 1:
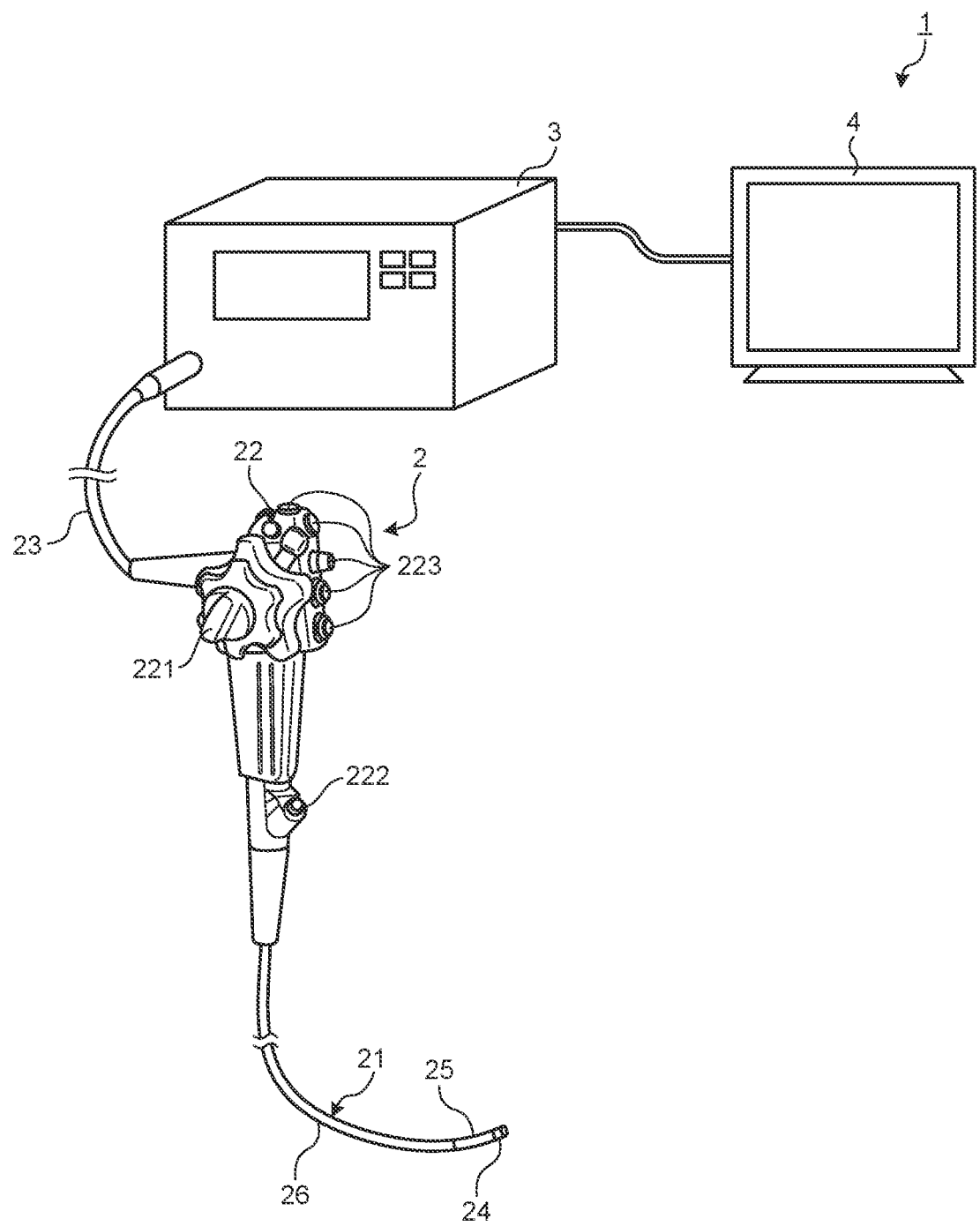
FIG. 1 is a diagram illustrating a schematic configuration of an endoscope system according to a first embodiment of the disclosure.
Figure 2:
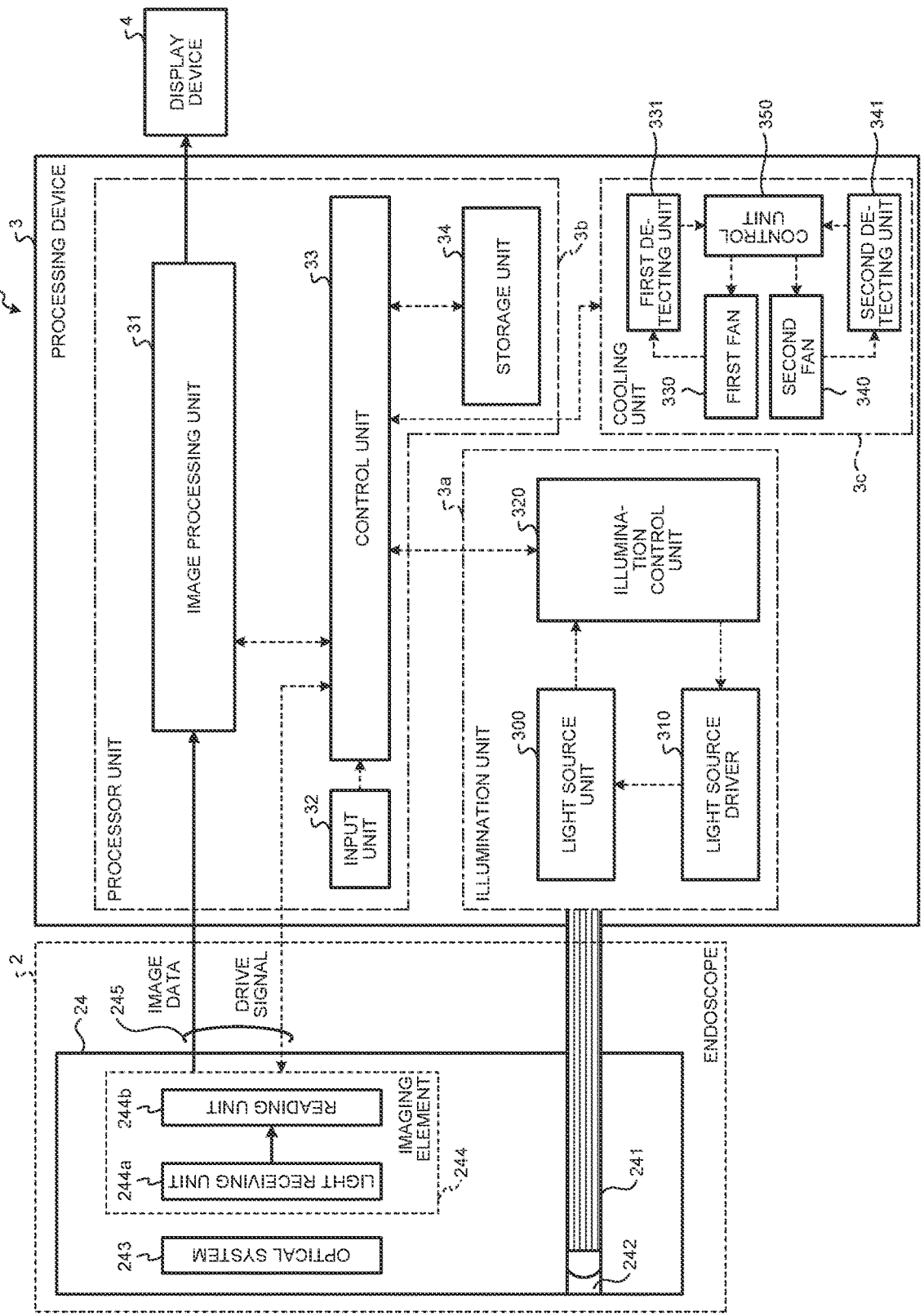
FIG. 2 is a block diagram illustrating a schematic configuration of the endoscope system according to the first embodiment of the disclosure.

FIG. 1 is a diagram illustrating a schematic configuration of an endoscope system according to a first embodiment of the disclosure. FIG. 2 is a block diagram illustrating a schematic configuration of the endoscope system according to the first embodiment.

An endoscope system 1 illustrated in FIG. 1 and FIG. 2 includes: an endoscope 2 that captures images inside a subject by insertion of a distal end portion of the endoscope 2 into the subject; a processing device 3 that has an illumination unit 3a, which generates illumination light to be emitted from a distal end of the endoscope 2, that performs predetermined signal processing on an imaging signal captured by the endoscope 2, and that integrally controls the overall operation of the endoscope system 1; and a display device 4 that displays an in-vivo image generated through the signal processing by the processing device 3.

The endoscope 2 includes: an insertion unit 21 that has flexibility and is elongated; an operating unit 22 that is connected to a proximal end of the insertion unit 21 and receives input of various operation signals; and a universal cord 23 that extends in a direction different from a direction, in which the insertion unit 21 extends from the operating unit 22, and that has various built-in cables for connection to the processing device 3 (including the illumination unit 3a).

The insertion unit 21 has: a distal end portion 24 having an imaging element 244 built therein, the imaging element 244 having two-dimensionally arrayed pixels that generate signals by receiving and photoelectrically converting light; a bending portion 25 that is formed of plural bending pieces and is freely bendable; and a flexible tube portion 26 that is connected to a proximal end of the bending portion 25, has flexibility, and is elongated. The insertion unit 21 is inserted into a body cavity of the subject, and captures, by means of the imaging element 244, an image of an object, such as body tissue at a position where external light is unable to reach.

The distal end portion 24 has: a light guide 241 that is formed by use of glass fiber and forms a light guiding path for light emitted by the illumination unit 3a; an illumination lens 242 that is provided at a distal end of the light guide 241; an optical system 243 for condensation; and the imaging element 244 (imaging unit) that is provided at an image forming position of the optical system 243, receives light condensed by the optical system 243, photoelectrically converts the light into an electric signal, and performs predetermined signal processing on the electric signal.

The optical system 243 is formed by use of one or plural lenses and has: an optical zooming function for change of the angle of view; and a focusing function for change of the focus.

The imaging element 244 generates an electric signal (image signal) by photoelectrically converting light from the optical system 243. Specifically, the imaging element 244 has: a light receiving unit 244a having plural pixels, which are arrayed in a matrix, each of which has a photodiode that accumulates electric charge according to quantity of light and a condenser that converts an electric charge transferred from the photodiode into a voltage level, and each of which generates an electric signal by photoelectrically converting light from the optical system 243; and a reading unit 244b that sequentially reads electric signals generated by pixels freely set as targets to be read, from the plural pixels of the light receiving unit 244a, and that outputs the read electric signals as image signals. The imaging element 244 is implemented by use of, for example, a charge coupled device (CCD) image sensor, or a complementary metal oxide semiconductor (CMOS) image sensor.

The endoscope 2 may have a memory (not illustrated in the drawings) that stores: an execution program and a control program, for the imaging element 244 to execute various operations; and data including identification information on the endoscope 2. The identification information includes, for example, unique information (ID), the model year, specification information, and the transmission scheme, of the endoscope 2.

The operating unit 22 has: a bending knob 221 that bends the bending portion 25 upward, downward, leftward, and/or rightward; a treatment tool insertion portion 222, through which treatment tools, such as biopsy forceps, an electric knife, and an examination probe, are inserted into the body cavity of the subject; and plural switches 223 serving as an operation input unit, through which peripheral device operating instruction signals are input, the peripheral device operating instruction signals being for, in addition to the processing device 3, a gas feeding means, a water feeding means, and screen display control, for example. A treatment tool inserted from the treatment tool insertion portion 222 comes out from an opening (not illustrated in the drawings) via a treatment tool channel (not illustrated in the drawings) in the distal end portion 24.

The universal cord 23 has, built therein, at least the light guide 241 and a cable assembly 245 formed of plural signal lines put together. The cable assembly 245 includes a signal line for transmission of imaging signals, a signal line for transmission of drive signals for driving the imaging element 244, and a signal line for transmission and reception of information including unique information related to the endoscope 2 (imaging element 244). According to the description of this embodiment, an electric signal is transmitted by use of a signal line, but an optical signal may be transmitted, or a signal may be transmitted between the endoscope 2 and the processing device 3 via wireless communication.

A configuration of the processing device 3 will be described next. The processing device 3 includes the illumination unit 3a, a processor unit 3b, and a cooling unit 3c. The cooling unit 3c corresponds to a cooling device.

A configuration of the illumination unit 3a will be described first. The illumination unit 3a includes a light source unit 300, a light source driver 310, and an illumination control unit 320.

The light source unit 300 includes one or plural light sources that emit light of a preset wavelength band, and an optical system that guides the light emitted by the light source/sources to the light guide 241.

The light source driver 310 causes, under control of the illumination control unit 320, the light source; sources to emit light, by supplying electric current to the light source/sources.

On the basis of a control signal (light control signal) from a control unit 33, the illumination control unit 320 controls the amount of electric power to be supplied to the light source/sources and controls drive timing for the light source/sources.

A configuration of the processor unit 3b will be described next. The processor unit 3b includes an image processing unit 31, an input unit 32, the control unit 33, and a storage unit 34.

The image processing unit 31 receives, from the endoscope 2, image data for illumination light of each color captured by the imaging element 242. In a case where the image processing unit 31 has received analog image data from the endoscope 2, the image processing unit 31 generates a digital imaging signal by performing A/D conversion. In a case where the image processing unit 31 has received image data as an optical signal, from the endoscope 2, the image processing unit 31 generates digital image data by performing photoelectric conversion.

The image processing unit 31 generates an image by performing predetermined image processing on image data received from the endoscope 2 and outputs the image to the display device 4. This predetermined image processing may include any of synchronization processing, gradation correction processing, and color correction processing. The image processing unit 31 generates an image signal including an in-vivo image generated by the image processing described above. The image processing unit 31 may perform gain adjustment according to brightness of the image. The image processing unit 31 is configured by use of a general-purpose processor, such as a central processing unit (CPU), or a special-purpose processor, such as an arithmetic circuit that executes a specific function, like an application specific integrated circuit (ASIC).

The input unit 32 is implemented by use of a keyboard and a mouse, switches, and/or a touch panel; and receives input of various signals, such as operation instruction signals for instructing the endoscope system 1 to operate. The input unit 32 may include a switch provided in the operating unit 22, or a portable terminal, such as an external tablet computer.

The control unit 33 controls driving of units including the imaging element 244 and the illumination unit 3a, and controls input and output of information to and from these units. The control unit 33 refers to control information data (for example, readout timing) for imaging control stored in the storage unit 34, and transmits the control information data as a drive signal to the imaging element 244 via a predetermined signal line included in the cable assembly 245. The control unit 33 is configured by use of: a general-purpose processor, such as a CPU; or a special-purpose processor, such as an arithmetic circuit that executes a specific function, like an ASIC.

The storage unit 34 stores therein various programs for operating the endoscope system 1, and data including various parameters needed for the operation of the endoscope system 1. The storage unit 34 also stores therein identification information on the processing device 3. This identification information includes, for example, unique information (ID), the model year, and specification information, of the processing device 3.

The storage unit 34 stores therein various programs including an image acquisition processing program for the processing device 3 to execute an image acquisition processing method. The various programs may be widely distributed by being recorded in a computer readable recording medium, such as a hard disk, a flash memory, a (CD-ROM, a DVD-ROM, or a flexible disk. These various programs may be acquired by being downloaded via a communication network. The communication network referred to herein is implemented by, for example, an existing public network, a local area network (LAN), or a wide area network (WAN, and may be wired or wireless.

The storage unit 34 configured as described above is implemented by use of: a read only memory (ROM) having the various programs installed therein beforehand; and a RAM or a hard disk storing therein arithmetic operation parameters and data for processing.

The display device 4 displays a display image corresponding to an image signal received from the processing device 3 (the image processing unit 31) via a video cable. The display device 4 is configured by use of a liquid crystal or organic electroluminescence (EL) monitor, for example.

Figure 3:
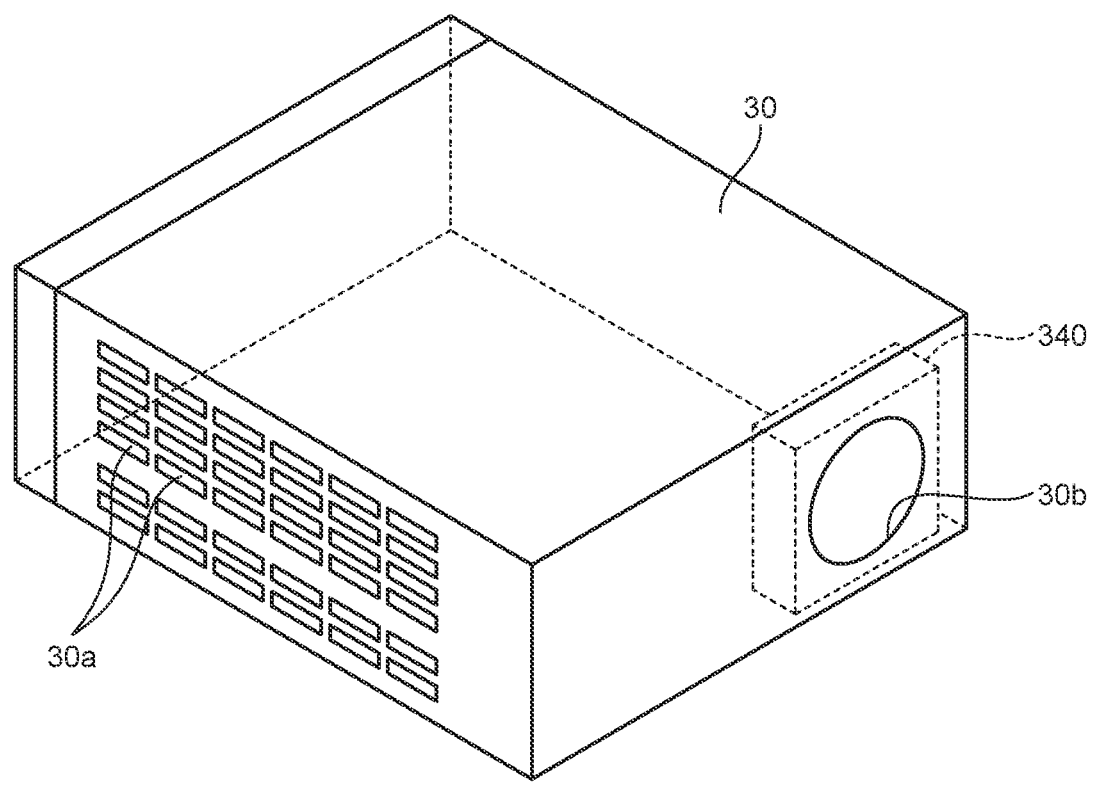
FIG. 3 is a diagram illustrating a configuration of a processing device included in the endoscope system according to the first embodiment of the disclosure.

A housing of the processing device 3 will be described by reference to FIG. 3. FIG. 3 is a diagram illustrating a configuration of a processing device included in the endoscope system according to the first embodiment of the disclosure. The processing device 3 is configured to have parts housed in a housing 30, which is a box. The housing 30 has, formed therein, a first communicating portion 30a for communication between the exterior and the interior of the housing 30, and a second communicating portion 30b. The first communicating portion 30a and the second communicating portion 30b are respectively formed on surfaces of the housing 30, the surfaces being different from each other and different from a surface of the housing 30, the surface being where the endoscope 2 is connected. A second fan 340, which will be described later, is provided inside the housing 30, at an opening of the second communicating portion 30b. By the second fan 340 being driven, air is suctioned from the first communicating portion 30a and air is released from the second communicating portion 30b.

Figure 4:
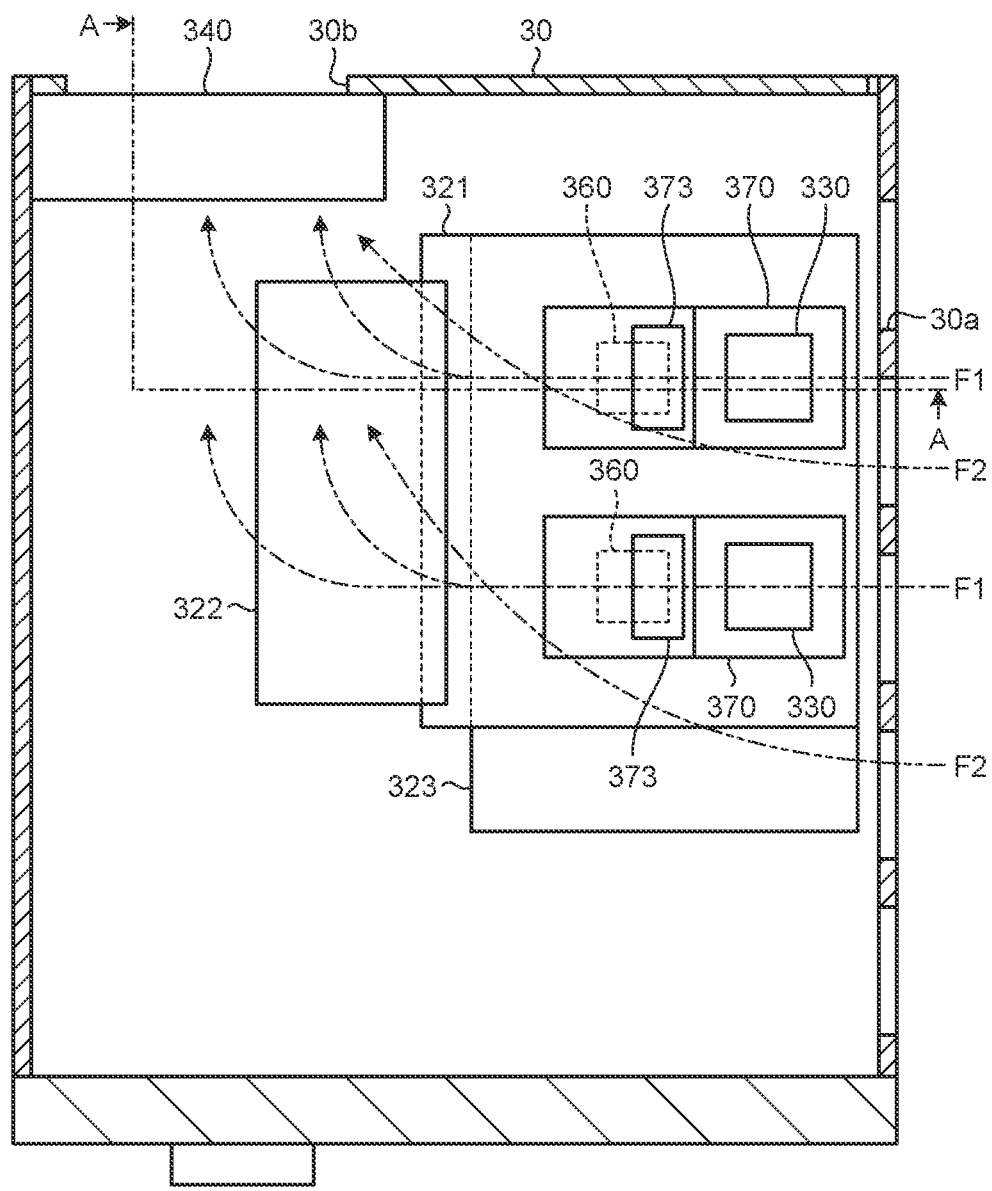
FIG. 4 is a diagram illustrating a configuration of a cooling unit provided in the processing device included the endoscope system according to the first embodiment of the disclosure.
Figure 5:
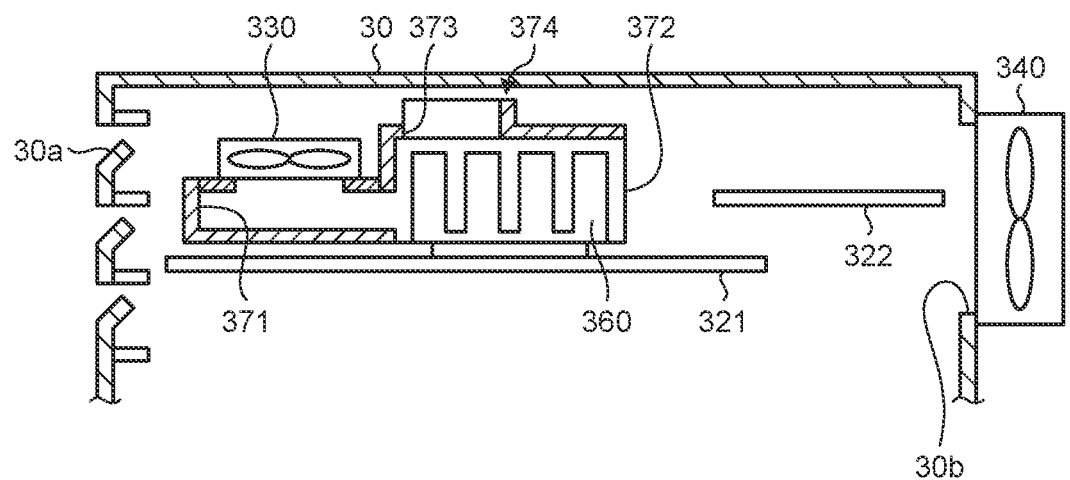
FIG. 5 is a partial sectional view of the cooling unit corresponding to a cross section cut by a line A-A illustrated in FIG. 4.

A configuration of the cooling unit 3c will be described next. FIG. 4 is a diagram illustrating a configuration of a cooling unit provided in the processing device included in the endoscope system according to the first embodiment of the disclosure. FIG. 5 is a partial sectional view of the cooling unit corresponding to a cross section cut by a line A-A illustrated in FIG. 4. The cooling unit 3c includes a first fan 330, a first detecting unit 331, a second fan 340, a second detecting unit 341, a control unit 350, a heatsink 360, and a duct 370.

The first far 330 and the second fan 340 generate airflows by being driven. The first fan 330 and the second fan 340 are arranged such that their blowing directions (the installation directions of their blades) are perpendicular to each other.

The first detecting unit 331 detects a driven state of the first fan 330 and outputs the driven state to the control unit 350.

The second detecting unit 341 detects a driven state of the second fan 340 and outputs the driven state to the control unit 350.

The first detecting unit 331 and the second detecting unit 341 acquire electric current values as the driven states and outputs the electric current values as detected values, to the control unit 350.

The control unit 350 controls driving of the first fan 330 and the second fan 340. The control unit 350 outputs detection results acquired from the first detecting unit 331 and the second detecting unit 341 to the control unit 33 and controls, on the basis of control signals from the control unit 33, driving of the first fan 330 and the second fan 340.

In a case where the control unit 350 determines, on the basis of a detected value from the first detecting unit 331, that the first fan 330 is stopped, the control unit 350 increases output (the number of rotations) of the second fan 340 to increase the airflow resulting from the second fan 340 being driven. On the contrary, in a case where the control unit 350 determines, on the basis of a detected value from the second detecting unit 341, that the second fan 340 is scooped, the control unit 350 increases output (the number of rotations) of the first fan 330 to increase the airflow resulting from the first fan 330 being driven. A threshold for determination of stoppage of driving is set beforehand, and the control unit 350 compares a detected value with this threshold to determine whether a fan as stopped. In a case where the number of rotations of a fan has become unable to be read, the control unit 350 increases the number of rotations of another fan other than that fan, of which the number of rotations is unable to be read.

The control unit 350 is configured by use of: a general-purpose processor, such as a CPU; or a special-purpose processor, such as an arithmetic circuit that executes a specific function, like an ASIC.

The heatsink 360 is provided on any of substrates 321 to 323 where circuits forming the control unit 33, the illumination control unit 320, and the control unit 350, for example, are mounted. FIG. 4 and FIG. 5 illustrate an example where the heatsink 360 is provided in a circuit mounted on the substrate 321. The heatsink 360 absorbs heat that is generated at the substrate 321, and releases the heat to the exterior. A heat generating element (for example, a circuit) on a substrate and the heatsink 360 in contact with this heating element correspond to a heat generator.

Figure 6:
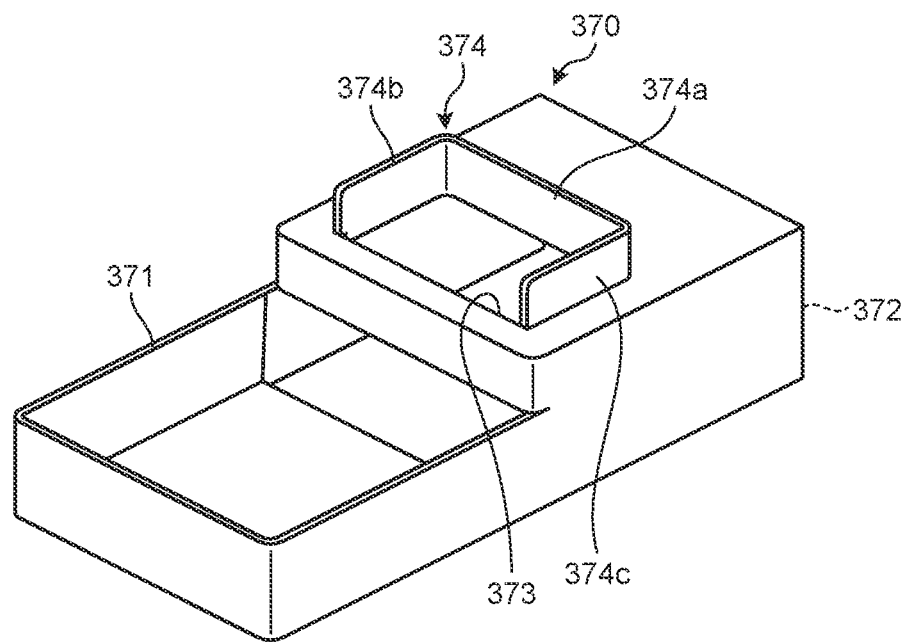
FIG. 6 is a perspective view illustrating a configuration of a duct provided in the processing device included in the endoscope system according to the first embodiment of the disclosure.
Figure 7:
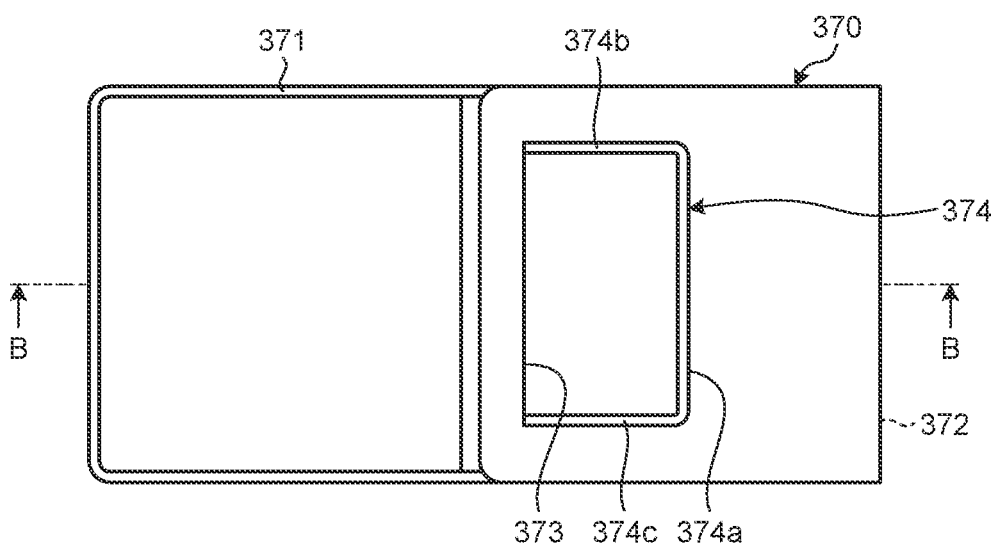
FIG. 7 is a plan view illustrating the configuration of the duct provided in the processing device included in the endoscope system according to the first embodiment of the disclosure.
Figure 8:
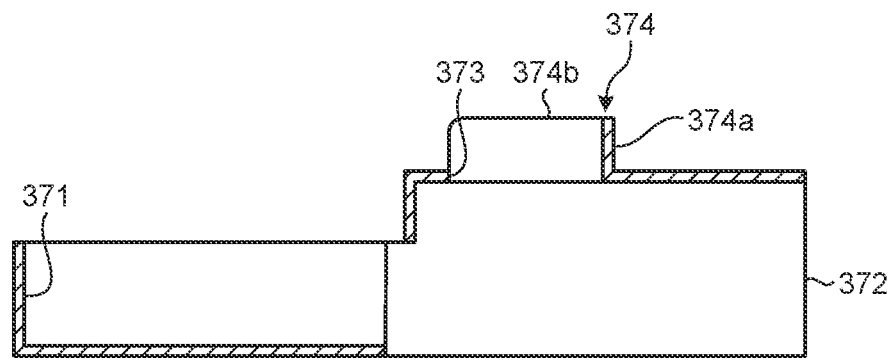
FIG. 8 is a sectional view taken upon a line B-B illustrated in FIG. 7.

FIG. 6 is a perspective view illustrating a configuration of a duct provided in the processing device included in the endoscope system according to the first embodiment of the disclosure. FIG. 7 is a plan view illustrating the configuration of the duct provided the processing device included in the endoscope system according to the first embodiment of the disclosure. FIG. 8 is a sectional view taken upon a line B-B illustrated in FIG. 7.

The duct 370 is provided on the substrate 321 and covers the heatsink 360. The duct 370 has a stepped box shape. A first opening 371, a second opening 372, and a third opening 373 are formed in the duct 370. The first opening 371, the second opening 372, and the third opening 373 each form an opening having an outer edge that is rectangular.

The first opening 371 is formed such that when the duct 370 is arranged on the substrate 321, the first opening 371 is positioned near the first communicating portion 30a. The second opening 372 is formed such that when the duct 370 is arranged on the substrate 321, the second opening 372 is positioned nearer to the second communicating portion 30b than the first opening 371 is. Specifically, along an airflow flowing from the first opening 371 to the second opening 372

(an airflow F1 described later), the second opening 372 is formed downstream from the heat generator. Furthermore, along the airflow flowing from the first opening 371 to the second opening 372, the second fan 340 is provided downstream from the second opening 372.

The first fan 330 is provided at the first opening 371. By the first fan 330 being driven, a flow an airflow) is able to be formed even more stably. This flow allows air to be taken into the duct 370 via the first opening 371 and to be released to the exterior of the duct 370 from the second opening 372.

The duct 370 is connected to the first fan 330. FIG. 5 illustrates an example where the duct 370 and the first fan 330 are physically in contact with each other, but as long as air is able to be taken into the duct 370 and an airflow is able to be generated by the first fan 330 being driven, the first fan 330 and the duct 370 may be configured to be not physically in contact with each other.

Along the airflow flowing from the first opening 371 to the second opening 372, the third opening 373 is provided downstream from the first opening 371. The third opening 373 is formed between the first opening 371 and the second opening 372. The third opening 373 is formed on a wall surface that does not intersect with a circulation route of air entering from the first opening 371 and being released from the second opening 372, and herein that wall surface faces the substrate 321.

A wall 374 is provided in a standing manner on the outer edge of the third opening 373 of the duct 370. The wall 374 extends outward from the duct 370. Specifically, the wall 374 extends perpendicularly to a surface where the third opening 373 is formed. A surface where an opening is formed herein refers to a duct surface having the outer edge formed by the opening.

In a plan view along a direction orthogonal to the surface where the third opening 373 is formed, the wall 374 has a U-shape. The bottom of the U-shape corresponds to part of the outer edge of the third opening 373, the part being near the second opening 372. Specifically, the wall 374 has: a first wall portion 374a provided near the second opening 372; a second wall portion. 374b extending from one end of the first wall portion 374a toward the first opening 371; and a third wall portion 374c extending from the other end of the first wall portion 374a toward the first opening 371. The second wall portion 374b and third wall portion 374c of the wall 374 are parallel to each other. An example where the wall 374 is provided on the outer edge of the third opening 373 is described herein, but as long as the wall 374 is in the vicinity including the outer edge of the opening of the third opening 373, the vicinity having a distance allowing air that has hit the wall 374 to be taken into the third opening 373, the wall 374 may be provided at a position separate from the outer edge of the opening of the third opening 373.

Figure 9:
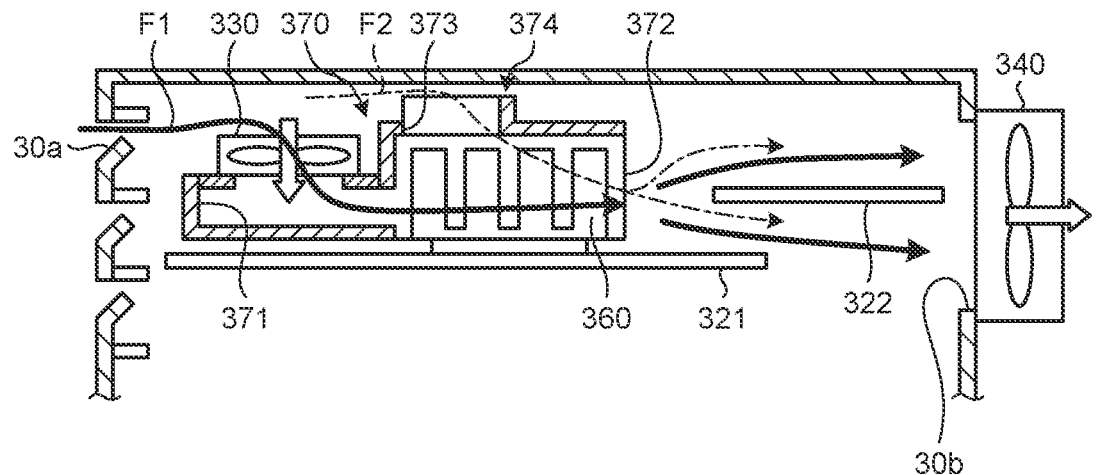
FIG. 9 is a diagram for explanation of airflows in the cooling device.

FIG. 9 is a diagram for explanation of airflows in the cooling device. In a case where the first fan 330 and the second fan 340 are being driven, the airflow F1 is generated in the housing 30. The airflow F1 enters the duct 370 from the first communicating portion 30a, passes through the heatsink 360, is released to the exterior of the duct 370 from the second opening 372, and is released to the exterior of the housing 30 via the second communicating portion 30b. This airflow F1 is generated by the first fan 330 being driven and forms a circulation route of air that passes through the first opening 371 and the second opening 372. This airflow F1 corresponds to a first airflow.

However, when the first fan 330 stops being driven, the flow of air entering the duct 370 from the first opening 371 becomes stagnant. When this happens, an airflow F2 is generated in the duct 370. In this airflow F2, air enters the duct 370 from the third opening 373 and is released from the second opening 372. The air in the airflow F2 collides with the wall 374 after entering the housing 30, flows toward the third opening 373, and enters the duct 370. This generation of the airflow F2 enables the flow of air via the heatsink 360 to be maintained even in a case where the first fan 330 stops being driven.

For the flow of air to be maintained, the third opening 373 is preferably formed at an upstream position near the heatsink 360 (heat generator). For example, the third opening 373 is provided such that the opening (hole) formed by the third opening 373 is provided at a position (see FIG. 4) including at least part of the heatsink 360 as viewed along the penetrating direction of the opening.

In the above described first embodiment, a configuration that releases the heat taken into the heatsink 360 to the exterior of the housing includes the third opening 373 and the wall 374 that are formed in the duct 370, through which air is sent to the heatsink 360. The third opening 373 is different from the first opening 371 where the first fan 330 is arranged, and the wall 374 is provided to stand externally from the third opening 373 to send air into the duct 370. The first embodiment enables efficient ventilation in the housing because air colliding with the wall 374 is taken into the duct 370 via the third opening 373 and passage of the air to the heatsink 360 is thus able to be maintained even in a case where the fan stops being driven.

First Modified Example of First Embodiment

Figure 10:
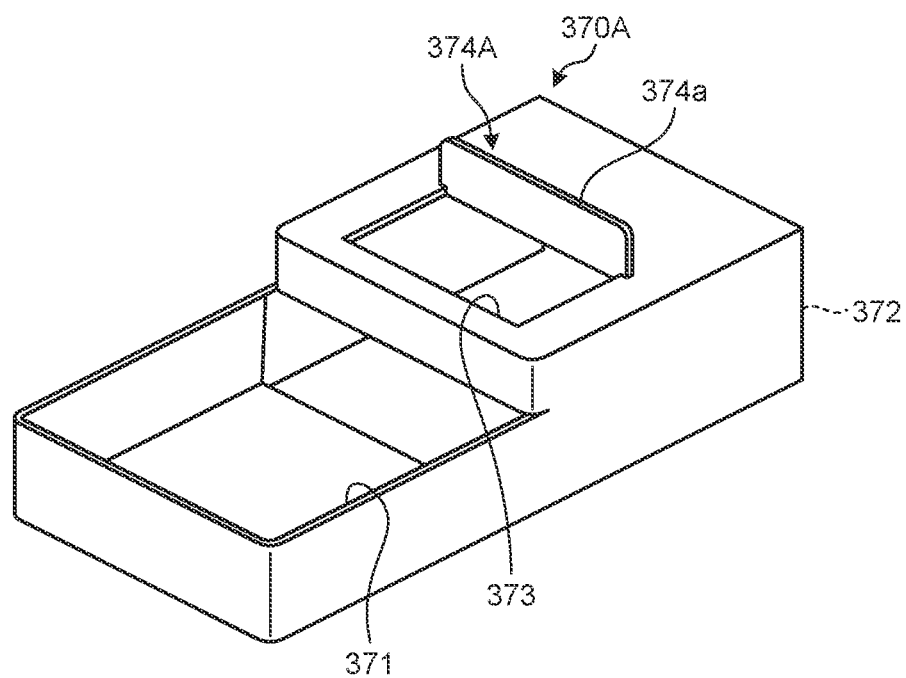
FIG. 10 is a perspective view illustrating a configuration of a duct provided in a processing device included in an endoscope system according to a first modified example of the first embodiment of the disclosure.
Figure 11:
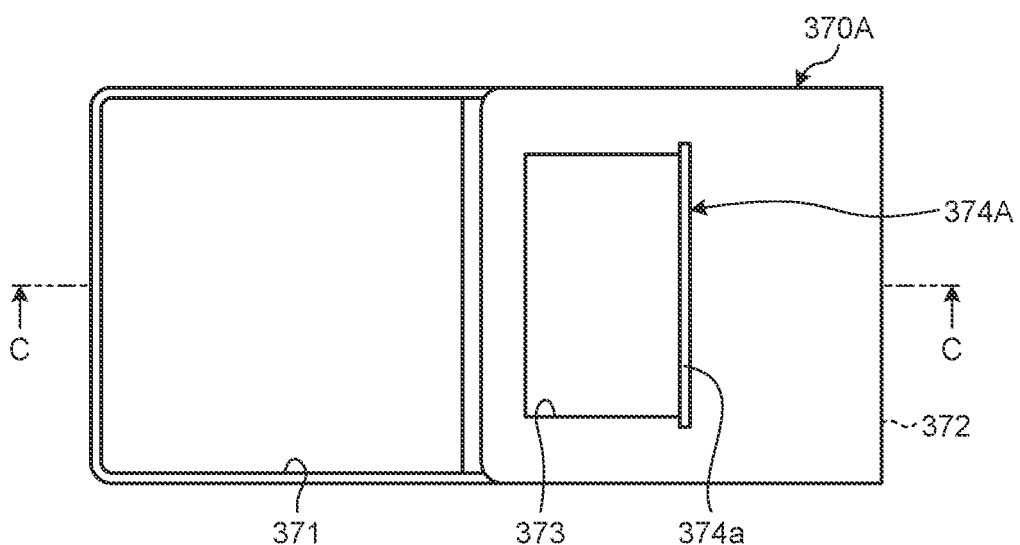
FIG. 11 is a plan view illustrating the configuration of the duct provided in the processing device included in the endoscope system according to the first modified example of the first embodiment of the disclosure.
Figure 12:
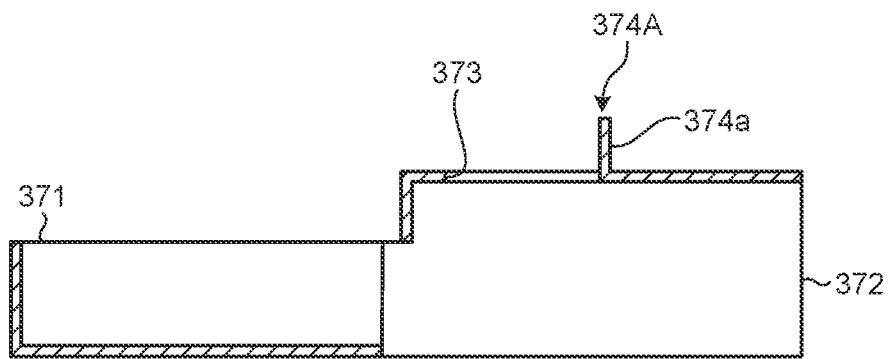
FIG. 12 is a sectional view taken upon a line C-C illustrated in FIG. 11.

A first modified example of the first embodiment of the disclosure will be described next by reference to FIG. 10 to FIG. 12. FIG. 10 is a perspective view illustrating a configuration of a duct provided in a processing device included in an endoscope system according to the first modified example of the first embodiment of the disclosure. FIG. 11 is a plan view illustrating the configuration of the duct provided in the processing device included in the endoscope system according to the first modified example of the first embodiment of the disclosure. FIG. 12 is a sectional view taken upon a line C-C illustrated in FIG. 11. The endoscope system according to the first modified example has the same configuration as the endoscope system described above, except that the endoscope system according to the first modified example has a duct 370A instead of the duct 370 of the endoscope system 1. The duct 370A having a configuration different from that of the first embodiment will thus be described hereinafter.

The duct 370A is provided on the substrate 321 and covers the heatsink 360, similarly to the duct 370. The duct 370A has a stepped box shape. A first opening 371, a second opening 372, and a third opening 373 are formed in the duct 370A.

A wall 374A is provided in a standing manner on an outer edge of the third opening 373 of the duct 370A. The wall 374A extends perpendicularly to a surface where the third opening 373 is formed. The wall 374A extends in a plate shape from the outer edge of the third opening, the outer edge being near the second opening 372. Specifically, the wall 374A is formed of the first wall portion 374a only.

In a case where the first fan 330 and the second fan 340 are being driven, the airflow F1 is generated in the housing 30 (see FIG. 9).

However, when the first fan 330 stops being driven, the flow of air entering the duct 370A from the first opening 371 becomes stagnant. When this happens, the airflow F2 (see FIG. 9) is generated in the duct 370A in this airflow F2, air enters the duct 370A from the third opening 373 and is released from the second opening 372. The air in the airflow F2 collides with the wall 374A after entering the housing 30, flows toward the third opening 373, and enters the duct 370A. Although the wall 374A is provided in the standing manner only on the outer edge near the second opening 372, the wall 374 enables air to be taken into the duct 370A by being formed at a position allowing air to collide with the wall 374A. This generation of the airflow F2 enables the flow of air via the heatsink 360 to be maintained even in a case where the first fan 330 stops being driven.

In the above described first modified example, a configuration that releases the heat taken into the heatsink 360 to the exterior of the housing includes the third opening 373 and the wall 374A that are formed in the duct 370A, through which air is sent to the heatsink 360. The third opening 373 is different from the first opening 371 where the first fan 330 is arranged, and the wall 374A is provided to stand externally from the third opening 373 to send air into the duct 370A. The first modified example enables efficient ventilation in the housing because air colliding with the wall 374A is taken into the duct 370A via the third opening 373 and passage of the air to the heatsink 360 is thus able to be maintained even in a case where the fan stops being driven.

Second Modified Example of First Embodiment

Figure 13:
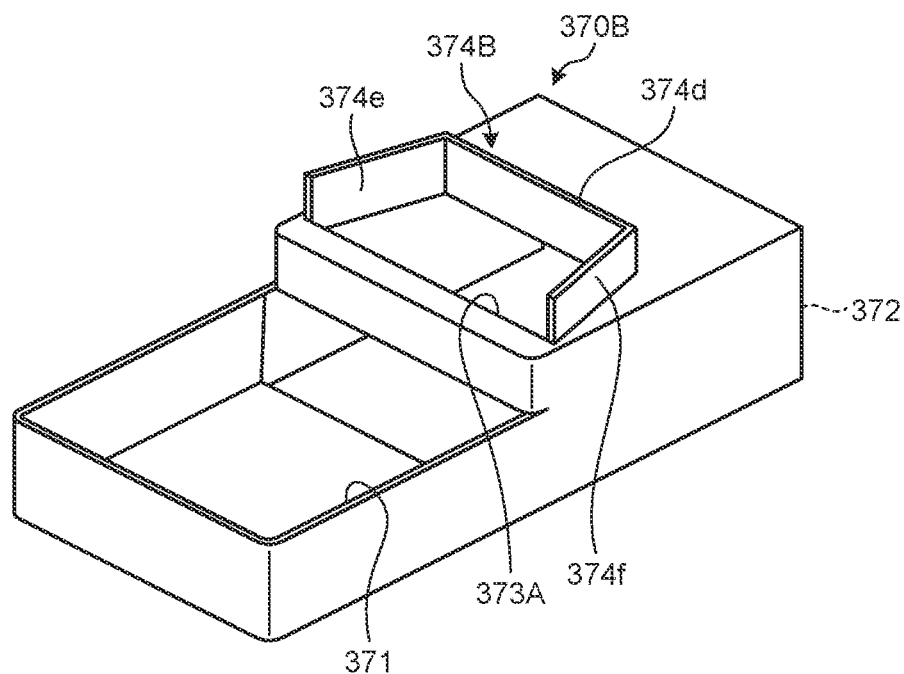
FIG. 13 is a perspective view illustrating a configuration of a duct provided in a processing device included in an endoscope system according to a second modified example of the first embodiment of the disclosure.
Figure 14:
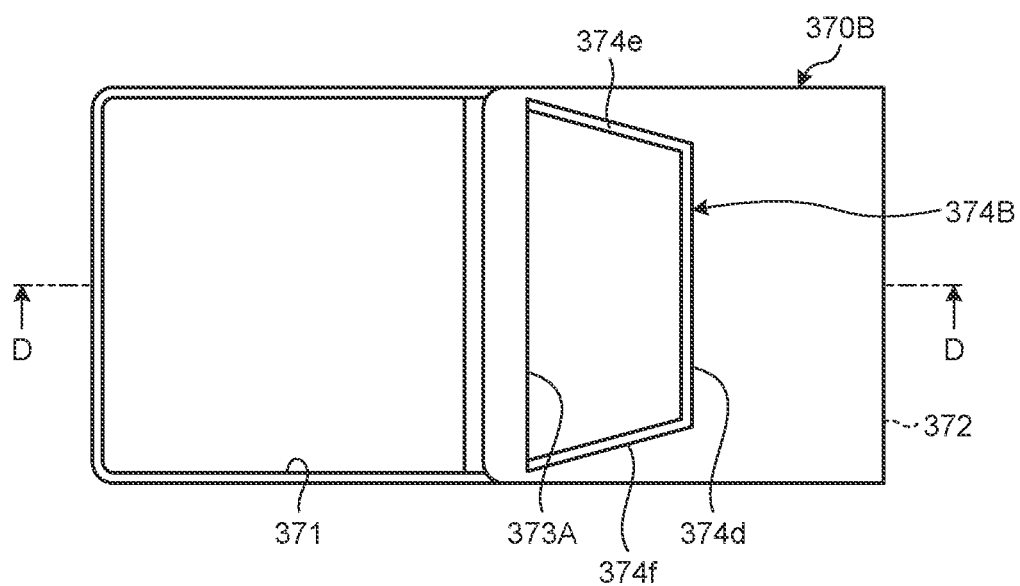
FIG. 14 is a plan view illustrating the configuration of the duct provided in the processing device included in the endoscope system according to the second modified example of the first embodiment of the disclosure.
Figure 15:
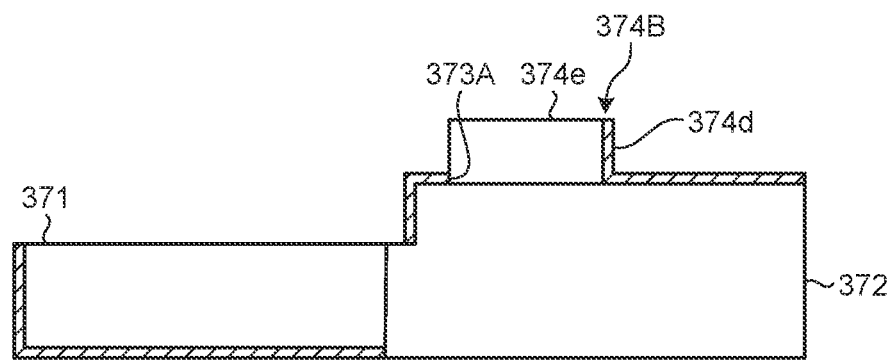
FIG. 15 is a sectional view taken upon a line D-D illustrated in FIG. 14.

A second modified example of the first embodiment of the disclosure will be described next by reference to FIG. 13 to FIG. 15. FIG. 13 is a perspective view illustrating a configuration of a duct provided in a processing device included in an endoscope system according to the second modified example of the first embodiment of the disclosure. FIG. 14 is a plan view illustrating the configuration of the duct provided in the processing device included in the endoscope system according to the second modified example of the first embodiment of the disclosure. FIG. 15 is a sectional view taken upon a line D-D illustrated in FIG. 14. The endoscope system according to the second modified example has the same configuration as the endoscope system 1 described above, except that the endoscope system according to the second modified example has a duct 370B instead of the duct 370 of the endoscope system 1. The duct 370B having a configuration different from that of the first embodiment will Thus be described hereinafter.

The duct 370B is provided on the substrate 321 and covers the heatsink 360, similarly to the duct 370. The duct 370B has a stepped box shape. A first opening 371, a second opening 372, and a third opening 373A are formed in the duct 370B.

The third opening 373A forms an opening having an outer edge that is trapezoidal. The shorter base of the trapezoid of the outer edge of the third opening 373A is positioned near the second opening 372.

A wall 374B is provided in a standing manner on the outer edge of the third opening 373A of the duct 370B. The wall 374B extends perpendicularly to a surface where the third opening 373A is formed. In a plan view along a direction orthogonal to the surface where the third opening 373A is formed, the wall 374B has a U-shape. The bottom of the U-shape corresponds to part (corresponding to the shorter base) of the outer edge of the third opening 373A, the part being near the second opening 372. Specifically, the wall 374B has: a first wall portion 374*d* provided near the second opening 372; a second wall portion 374*e* extending from one end of the first wall portion 374*d* toward the first opening 371; and a third wall portion 374*f* extending from the other end of the first wall portion 374*d* toward the first opening 371.

In a case where the first fan 330 and the second fan 340 are being driven, the airflow F1 is generated in the housing 30 (see FIG. 9).

However, when the first fan 330 stops being driven, the flow of air entering the duct 3702 from the first opening 371 becomes stagnant. When this happens, the airflow F2 (see FIG. 9) is generated in the duct 370B. In this airflow F2, air enters the duct 3702 from the third opening 373A and is released from the second opening 372. The air in the airflow F2 collides with the wall 374B after entering the housing 30, flows toward the third opening 373A, and enters the duct 370B. Forming the wall 374B at a position allowing air taken into the housing 30 to collide with the wall 374B enables the air to be sent into the duct 370B. This generation of the airflow 22 enables the flow of air via the heatsink 360 to be maintained even in a case where the first fan 330 stops being driven.

In the above described second modified example, a configuration that releases the heat taken into the heatsink 360 to the exterior of the housing includes the third opening 373A and the wall 374B that are formed in the duct 370B, through which air is sent to the heatsink 360. The third opening 373A is different from the first opening 371 where the first fan 330 is arranged, and the wall 374B is provided to stand externally from the third opening 373A to send air into the duct 370A. The second modified example enables efficient ventilation in the housing because air colliding with the wall 374B is taken into the duct 370B via the third opening 373A and passage of the air to the heatsink 360 is thus able to be maintained even in a case where the fan stops being driven.

Third Modified Example of First Embodiment

Figure 16:
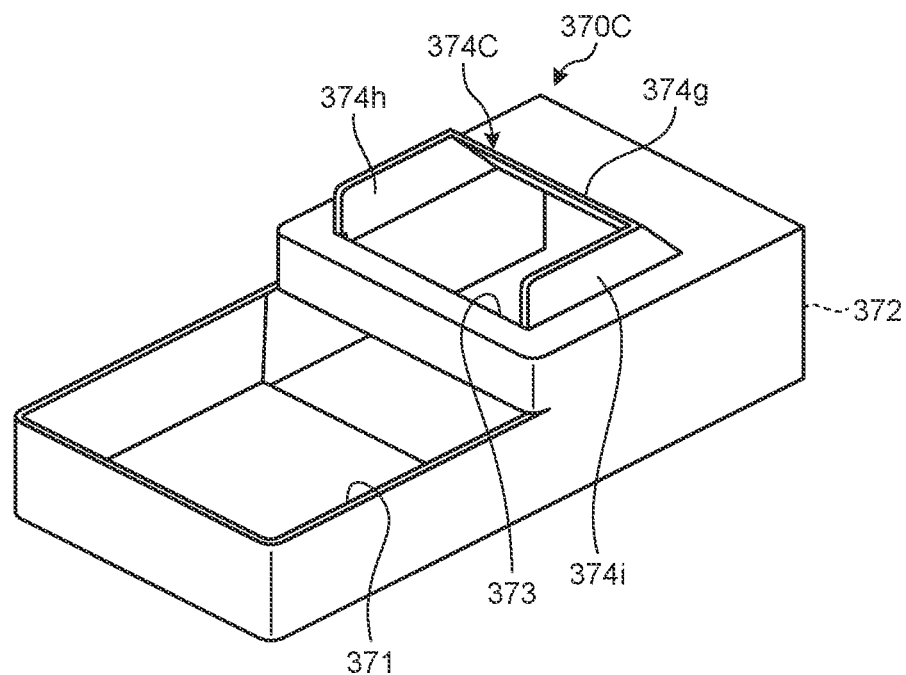
FIG. 16 is a perspective view illustrating a configuration of a duct provided in a processing device included in an endoscope system according to a third modified example of the first embodiment of the disclosure.
Figure 17:
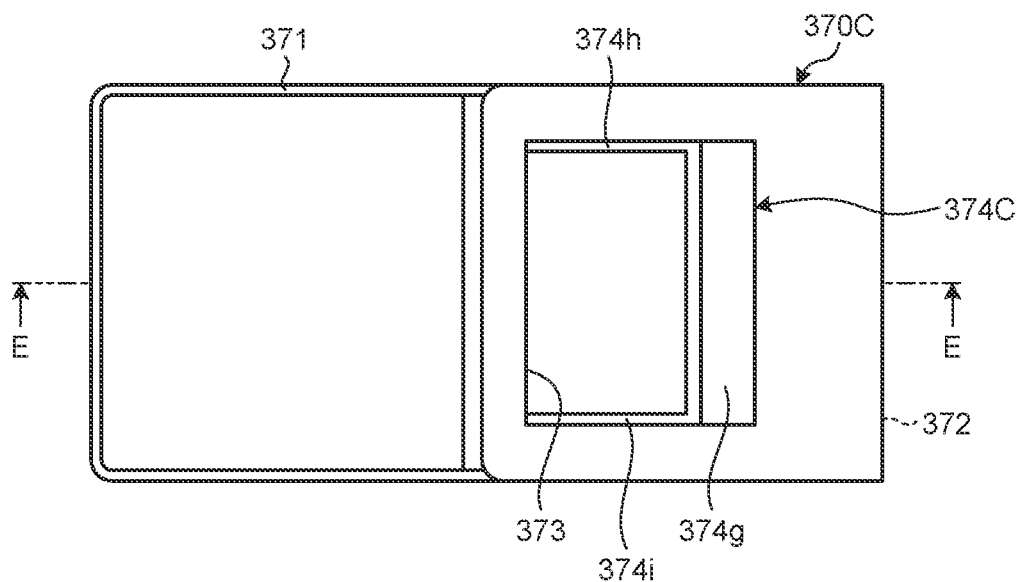
FIG. 17 is a plan view illustrating the configuration of the duct provided in the processing device included in the endoscope system according to the third modified example of the first embodiment of the disclosure.
Figure 18:
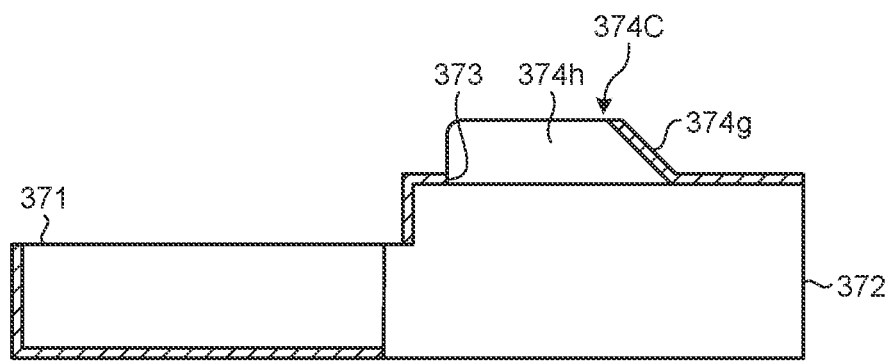
FIG. 18 is a sectional view taken upon a line E-E illustrated in FIG. 17.

A third modified example of the first embodiment of the disclosure will be described next by reference to FIG. 16 to FIG. 18. FIG. 16 is a perspective view illustrating a configuration of a duct provided in a processing device included in an endoscope system according to the third modified example of the first embodiment of the disclosure. FIG. 17 is a plan view illustrating the configuration of the duct provided in the processing device included in the endoscope system according to the third modified example of the first embodiment of the disclosure. FIG. 18 is a sectional view taken upon a line E-E illustrated in FIG. 17. The endoscope system according to the third modified example has the same configuration as the endoscope system 1 described above, except that the endoscope system according to the third modified example has a duct 370C Instead of the duct 370 of the endoscope system 1. The duct 370C having a configuration different from that of the first embodiment will thus be described hereinafter.

The duct 370C is provided on the substrate 321 and covers the heatsink 360, similarly to the duct 370. The duct 370C has a stepped box shape. A first opening 371, a second opening 372, and a third opening 373 are formed in the duct 370C.

A wall 374C is provided in a standing manner on an outer edge of the third opening 373 of the duct 370C. The wall 374C extends perpendicularly to a surface where the third opening 373 is formed in a plan view along a direction orthogonal to the surface where the third opening 373 is formed, the wall 3745 has a U-shape. The bottom of the U-shape corresponds to part of the outer edge of the third opening 373, the part being near the second opening 372. Specifically, the wall 374C has: a first wall portion 374g provided near the second opening 372; a second wall portion 374h extending from one end of the first wall portion 374g toward the first opening 371; and a third wall portion 374i extending from the other end of the first wall portion 374g toward the first opening 371. The first wall portion 374g is inclined toward the first opening 371 with respect to the surface where the third opening 373 is formed. Furthermore, the second wall portion 374h and the third wall portion 374i extend perpendicularly to the surface where the third opening 373 is formed.

In a case where the first fan 330 and the second fan 340 are being driven, the airflow F1 is generated in the housing 30 (see FIG. 9).

However, when the first fan 330 stops being driven, the flow of air entering the duct 370C from the first opening 371 becomes stagnant. When this happens, the airflow F2 (see FIG. 9) is generated in the duct 370C. In this airflow F2, air enters the duct 370C from the third opening 373 and is released from the second opening 372. The air in the airflow F2 collides with the wall 374C after entering the housing 30, flows toward the third opening 373, and enters the duct 370C. Forming the wall 374C at a position allowing air taken into the housing 30 to collide with the wall 374C enables the air to be sent into the duct 370C. This generation of the airflow F2 enables the flow of air via the heatsink 360 to be maintained even in a case where the first fan 330 stops being driven.

In the above described third modified example, a configuration that releases the heat taken into the heatsink 360 to the exterior of the housing includes the third opening 373 and the wall 374C that are formed in the duct 370C, through which air is sent to the heatsink 360. The third opening 373 is different from the first opening 371 where the first fan 330 is arranged, and the wall 374C is provided to stand externally from the third opening 373 to send air into the duct 370C. The third modified example enables efficient ventilation in the housing because air colliding with the wall 374C is taken into the duct 370C via the third opening 373 and passage of the air to the heatsink 360 is thus able to be maintained even in a case where the fan stops being driven.

Furthermore, the third modified example enables external air to be more efficiently taken into the duct 370C than the configuration of the first embodiment, for example, the configuration having the first wall portion extending perpendicularly to the surface where the third opening is formed, because the first wall portion 374g in the third modified example is inclined to approach the third opening 373.

Fourth Modified Example of First Embodiment

Figure 19:
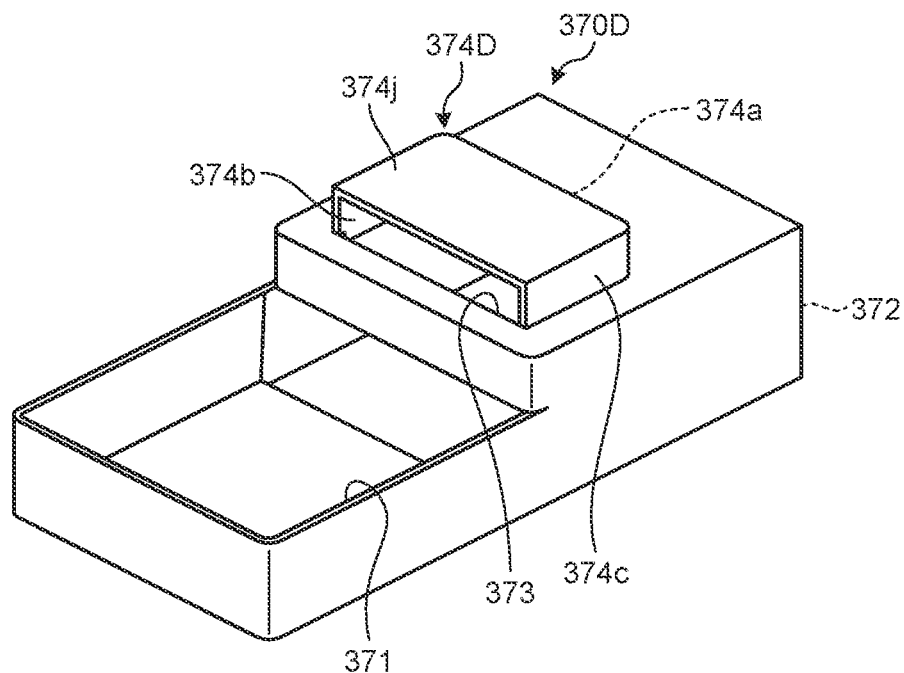
FIG. 19 is a perspective view illustrating a configuration of a duct provided in a processing device included in as endoscope system according to a fourth modified example of the first embodiment of the disclosure.
Figure 20:
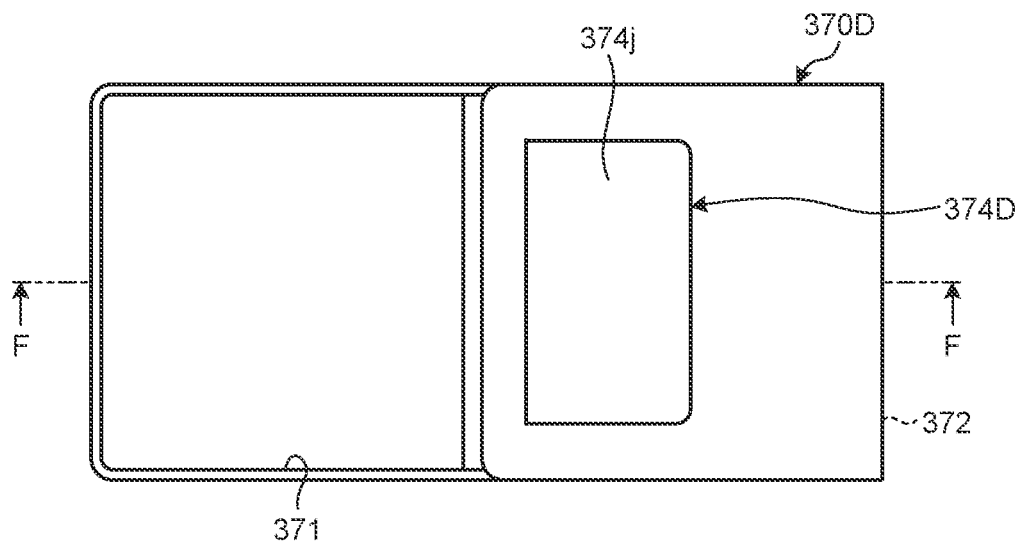
FIG. 20 is a plan view illustrating the configuration of the duct provided in the processing device included in the endoscope system according to the fourth modified example of the first embodiment of the disclosure.
Figure 21:
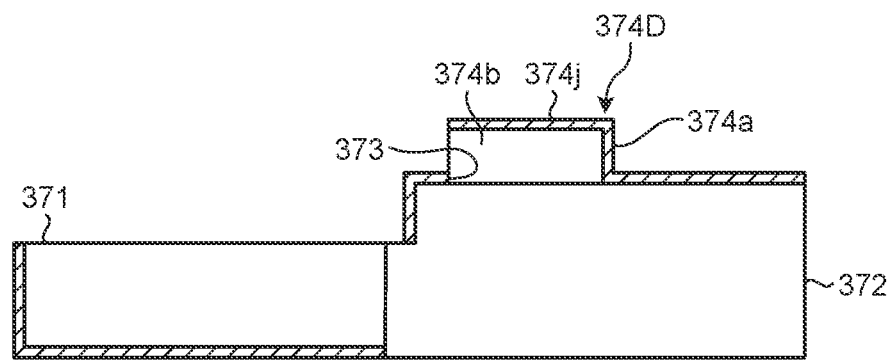
FIG. 21 is a sectional view taken upon a line F-F illustrated in FIG. 20.

A fourth modified example of the first embodiment of the disclosure will be described next by reference to FIG. 19 to FIG. 21. FIG. 19 is a perspective view illustrating a configuration of a duct provided in a processing device included in an endoscope system according to the fourth modified example of the first embodiment of the disclosure. FIG. 20 is a plan view illustrating the configuration of the duct provided in the processing device included in the endoscope system according to the fourth modified example of the first embodiment of the disclosure. FIG. 21 is a sectional view taken upon a line F-F illustrated in FIG. 20. The endoscope system according to the fourth modified example has the same configuration as the endoscope system 1 described above, except that the endoscope system according to the fourth modified example has a duct 370D instead of the duct 370 of the endoscope system 1. The duct 370D having a configuration different from that of the first embodiment will thus be described hereinafter.

The duct 370D is provided on the substrate 321 and covers the heatsink 360, similarly to the duct 370. The duct 370D has a stepped box shape. A first opening 371, a second opening 372, and a third opening 373 are formed in the duct 370D.

A wall 374D is provided in a standing manner on an outer edge of the third opening 373 of the duct 370D. The wall 374D has: a first wall portion 374a provided near the second opening 372; a second wall portion 374b extending from one end of the first wall portion 374a toward the first opening 371; a third wall portion 374c extending from the other end of the first wall portion 374a toward the first opening 371; and a lid portion 374j that is connected to opposite edges of the first wall portion 374a, second wall portion 374b, and third wall portion 374c and covers the third opening 373, the opposite edges being opposite to edges of the first wall portion 374a, second wall portion 374b, and third wall portion 374c, the edges being connected to the third opening 373. The wall 374D has a configuration having the lid portion 374j provided in the wall 374 described above.

In a case where the first fan 330 and the second fan 340 are being driven, the airflow F1 is generated in the housing 30 (see FIG. 9).

However, when the first fan 330 stops being driven, the flow of air entering the duct 370D from the first opening 371 becomes stagnant. When this happens, the airflow 12 (see FIG. 9) is generated in the duct 370D. In this airflow F2, air enters the duct 370D from the third opening 373 and is released from the second opening 372. The air in the airflow 12 collides with the wall 374D after entering the housing 30, flows toward the third opening 373, and enters the duct 370D. Intake of air by means of the wall 374D enables air to be sent into the duct 370D. This generation of the airflow 12 enables the flow of air via the heatsink 360 to be maintained even in a case where the first fan 330 stops being driven.

In the above described fourth modified example, a configuration that releases the heat taken into the heatsink 360 to the exterior of the housing includes the third opening 373 and the wall 374D that are formed in the duct 370D, through which air is sent to the heatsink 360. The third opening 373 is different from the first opening 371 where the first fan 330 is arranged, and the wall 374D is provided to stand externally from the third opening 373 to send air into the duct 370D. The fourth modified example enables efficient ventilation in the housing because air colliding with the wall 374D is taken into the duct 370D via the third opening 373 and passage of the air to the heatsink 360 is thus able to be maintained even in a case where the fan stops being driven.

Furthermore, the fourth modified example enables external air to be even more efficiently taken into the duct 370D because the wall 374D has the lid portion 374j and this lid portion 374j infallibly enables air passing above the third opening 373 to be taken into the duct 370D.

Fifth Modified Example of First Embodiment

Figure 22:
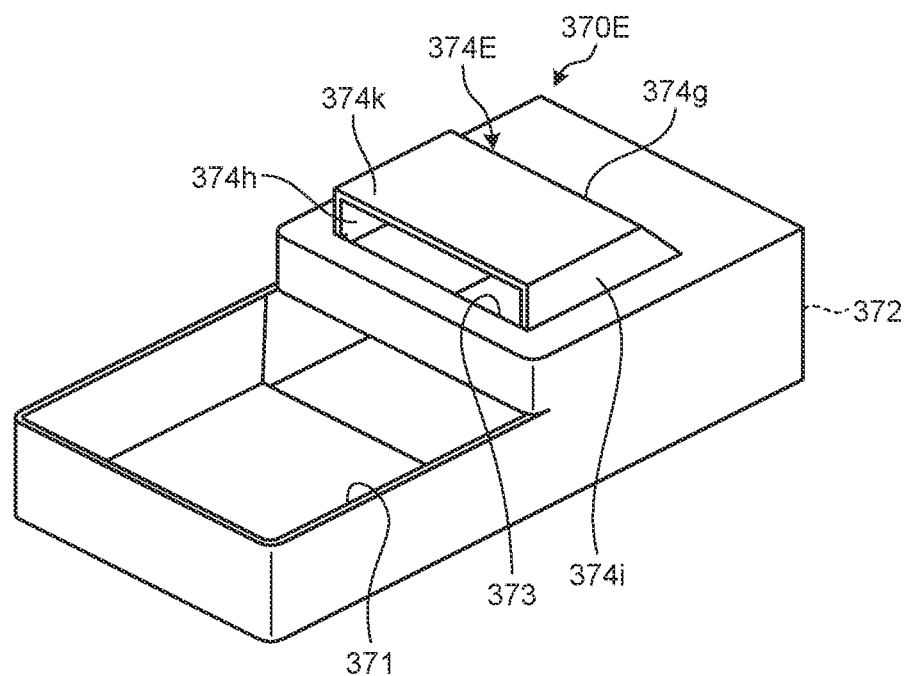
FIG. 22 is a perspective view illustrating a configuration of a duct provided in a processing device included in an endoscope system according to a fifth modified example of the first embodiment of the disclosure.
Figure 23:
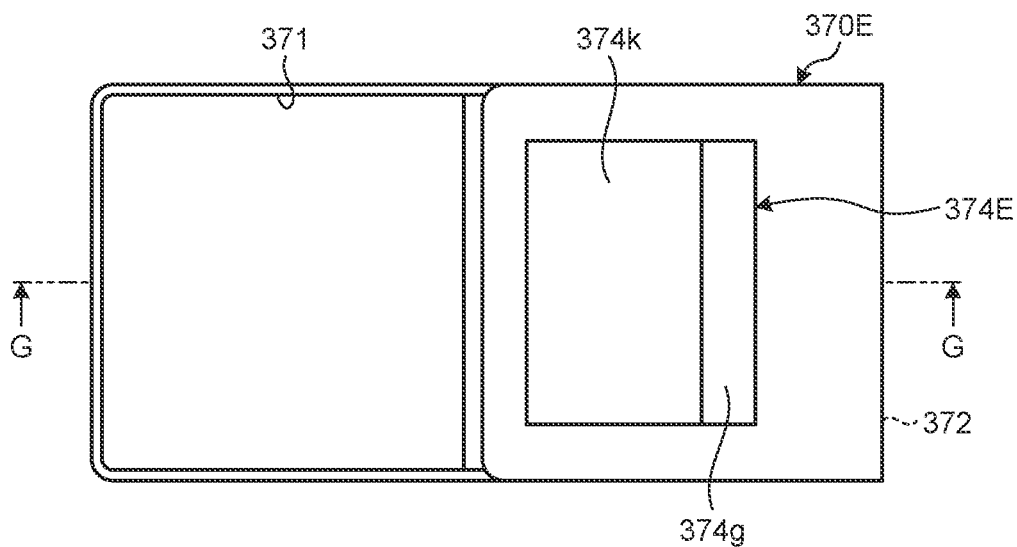
FIG. 23 is a plan view illustrating the configuration of the duct provided in the processing device included in the endoscope system according to the fifth modified example of the first embodiment of the disclosure.
Figure 24:
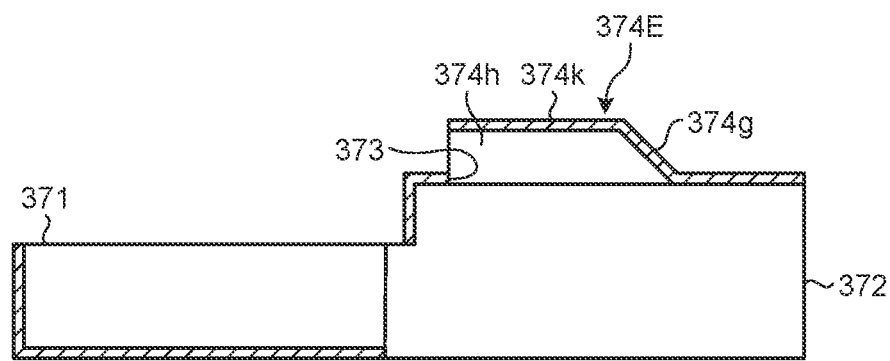
FIG. 24 is a sectional view taken upon a line G-G illustrated in FIG. 23.

A fifth modified example of the first embodiment of the disclosure will be described next by reference to FIG. 22 to FIG. 24. FIG. 22 is a perspective view illustrating a configuration of a duct provided in a processing device included in an endoscope system according to the fifth modified example of the first embodiment of the disclosure. FIG. 23 is a plan view illustrating the configuration of the duct provided in the processing device included in the endoscope system according to the fifth modified example of the first embodiment of the disclosure. FIG. 23 is a sectional view taken upon a line G-G illustrated in FIG. 22. The endoscope system according to the fifth modified example has the same configuration as the endoscope system 1 described above, except that the endoscope system according to the fifth modified example has a duct 370E instead of the duct 370 of the endoscope system 1. The duct 370E having a configuration different from that of the first embodiment will thus be described hereinafter.

The duct 370E is provided on the substrate 321 and covers the heatsink 360, similarly to the duct 370. The duct 370*k* has a stepped box shape. A first opening 371, a second opening 372, and a third opening 373 are formed in the duct 370E.

A wall 374E is provided in a standing manner on an outer edge of the third opening 373 of the duct 370E. The wall 374E has: a first wall portion 374*g* provided near the second opening 372; a second wall portion 374*h* extending from one end of the first wall portion 374*g* toward the first opening 371; a third wall portion 374*i* extending from the other end of the first wall portion 374*g* toward the first opening 371; and a lid portion 374*k* that is connected to opposite edges of the first wall portion 374*g*, second wall portion 374*h*, and third wall portion 374*i* and covers the third opening 373, the opposite edges being opposite to edges of the first wall portion 374*g*, second wall portion 374*h*, and third wall portion 374*i*, the edges being connected to the third opening 373. The wall 374E has a configuration having the lid portion 374*k* provided in the wall 374C described above.

In a case where the first fan 330 and the second fan 340 are being driven, the airflow F1 is generated in the housing 30 (see FIG. 9).

However, when the first fan 330 stops being driven, the flow of air entering the duct 370E from the first opening 371 becomes stagnant. When this happens, the airflow 12 (see FIG. 9) is generated in the duct 370E. In this airflow F2, air enters the duct 370E from the third opening 373 and is released from the second opening 372. The air in the airflow F2 collides with the wall 374E after entering the housing 30, flows toward the third opening 373, and enters the duct 370E. Forming the wall 374E at a position allowing air taken into the housing 30 to collide with the wall 374E enables the air to be sent into the duct 370E. This generation of the airflow 12 enables the flow of air via the heatsink 360 to be maintained even in a case where the first fan 330 stops being driven.

In the above described fifth modified example, a configuration that releases the heat taken into the heatsink 360 to the exterior of the housing includes the third opening 373 and the wall 374E that are formed in the duct 370E, through which air is sent to the heatsink 360. The third opening 373 is different from the first opening 371 where the first fan 330 is arranged, and the wall 374E is provided to stand externally from the third opening 373 to send air into the duct 370E. The fifth modified example enables efficient ventilation in the housing because air colliding with the wall 374E is taken into the duct 370E via the third opening 373 and passage of the air to the heatsink 360 is thus able to be maintained even in a case where the fan stops being driven.

Furthermore, the fifth modified example enables external air to be even more efficiently taken into the duct 370E because the wall 374E has the lid portion 374*k* and this lid portion 374*k* infallibly enables air passing above the third opening 373 to be taken into the duct 370E.

Second Embodiment

Figure 25:
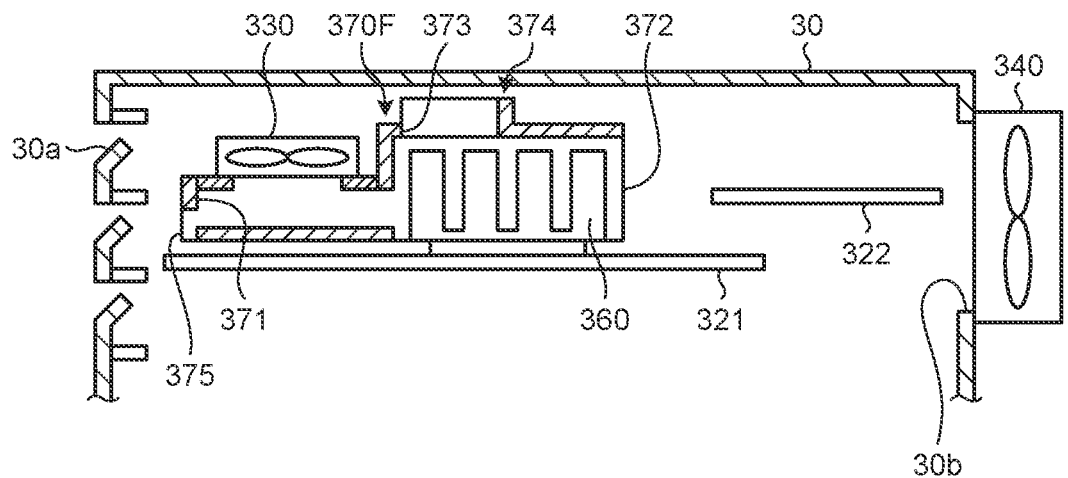
FIG. 25 is a diagram illustrating a configuration of a cooling unit provided in a processing device included in an endoscope system according to a second embodiment of the disclosure.
Figure 26:
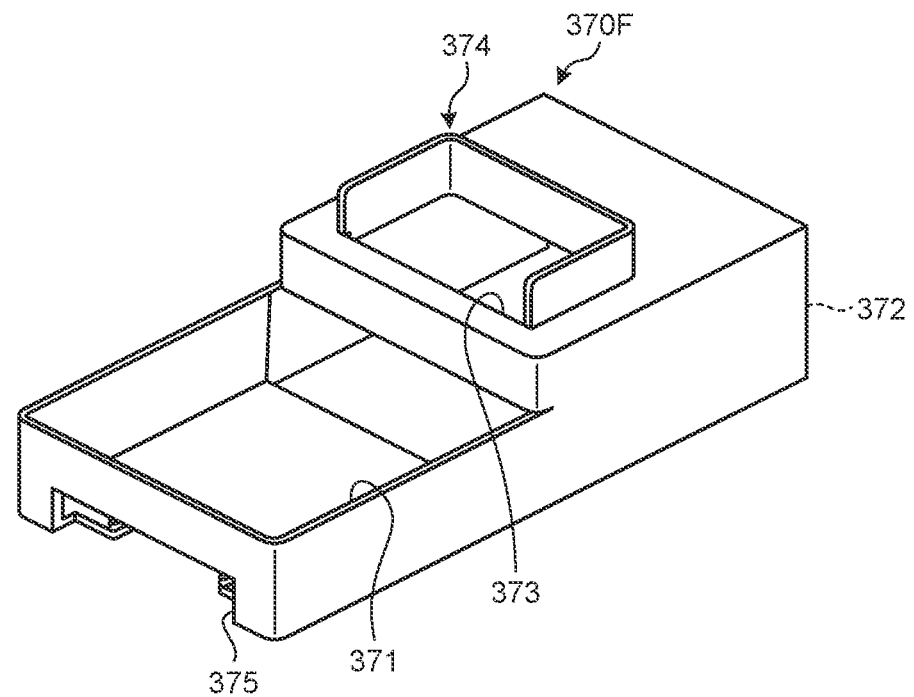
FIG. 26 is a perspective view illustrating a configuration of a duct provided in the processing device included in the endoscope system according to the second embodiment of the disclosure.

A second embodiment of the disclosure will be described next by reference to FIG. 25 and FIG. 26. FIG. 25 is a diagram illustrating a configuration of a cooling unit provided in a processing device included in an endoscope system according to the second embodiment of the disclosure. FIG. 26 is a perspective view illustrating a configuration of a duct provided in the processing device included in the endoscope system according to the second embodiment of the disclosure. The endoscope system according to the second embodiment has the same configuration as the endoscope system 1 described above, except that the endoscope system according to the second embodiment has a duct 370F instead of the duct 370 of the endoscope system 1. The duct 370F having a configuration different from that of the first embodiment will thus be described hereinafter.

The duct 370F is provided on the substrate 321 and covers the heatsink 360, similarly to the duct 370. The duct 370F has a stepped box shape. A first opening 371, a second opening 372, a third opening 373, and a fourth opening 375 are formed in the duct 370F. The fourth opening 375 forms an opening having an outer edge that is rectangular. A wall 374 is provides in a standing manner on an outer edge of the third opening 373 of the duct 370F.

The fourth opening 375 is formed such that when the duct 370F is arranged on the substrate 321, the fourth opening 375 is positioned near the first communicating portion 30*a*. Specifically, the fourth opening 375 is formed upstream of the first opening 371, along a circulation route of air (for example, the airflow F1) in the duct 370F.

In a case where the first fan 330 and the second fan 340 are being driven, the airflow F1 is generated in the housing 30 (see FIG. 9).

However, when the first fan 330 stops being driven, the flow of air entering the duct 370F from the first opening 371 becomes stagnant. When this happens, the airflow F2 (see FIG. 9) is generated in the duct 370F in this airflow F2, air enters the duct 370F from the third opening 373 and is released from the second opening 372. The air in the airflow F2 collides with the wall 374 after entering the housing 30, flows toward the third opening 373, and enters the duct 370F. Intake of air by means of the wall 374 enables air to be sent into the duct 370F. This generation of the airflow F2 enables the flow of air via the heatsink 360 to be maintained even in a case where the first fan 330 stops being driven.

Air is also taken into the duct 370F from the fourth opening 375. Therefore, as compared to the case where air is taken in from the third opening 373 only, the amount of air that is able to be taken into the duct 370F is increased and the amount of passed through the heatsink 360 is thus able to be increased.

In the above described second embodiment, a configuration that releases the heat taken into the heatsink 360 to the exterior of the housing includes the third opening 373 and the wall 374 that are formed in the duct 370F, through which air is sent to the heatsink 360. The third opening 373 is different from the first opening 371 where the first fan 330 is arranged, and the wall 374 is provided to stand externally from the third opening 373 to send air into the duct 370F. The second embodiment enables, similarly to the first embodiment, efficient ventilation in the housing because air colliding with the wall 374 is taken into the duct 370F via the third opening 373 and passage of the air to the heatsink 360 is thus able to be maintained even in a case where the fan stops being driven.

The second embodiment also enables increase in the amount of air passing through the duct 370F and even more efficient cooling of the heatsink 360 because the fourth opening 375 is formed in the duct 370F and air is able to be taken into the duct 370F additionally from this fourth opening 375.

Modified Example of Second Embodiment

Figure 27:
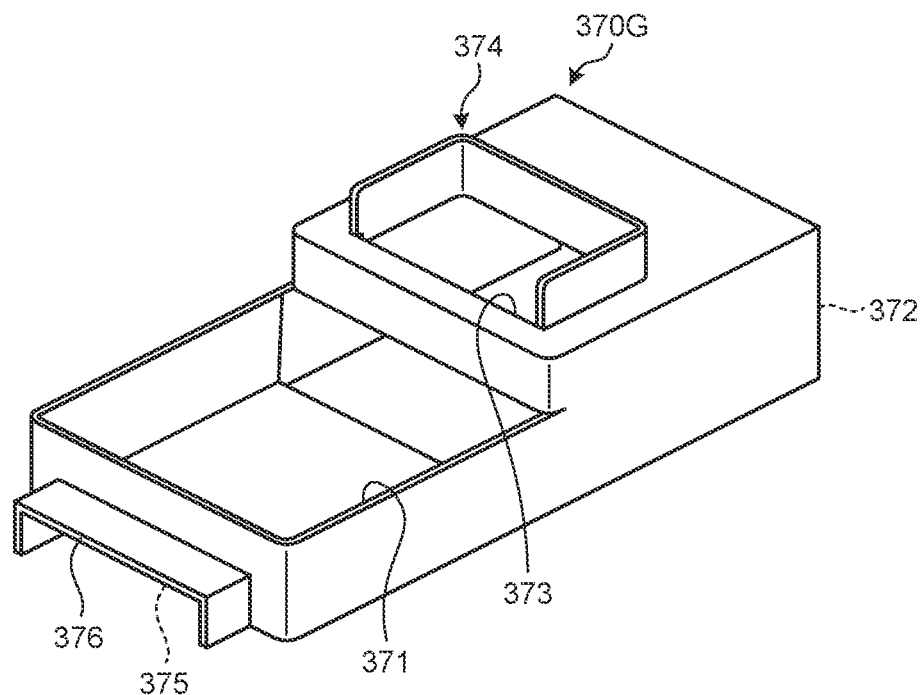
FIG. 27 is a perspective view illustrating a configuration of a duct provided in a processing device included in an endoscope system according to a modified example of the second embodiment of the disclosure.
Figure 28:
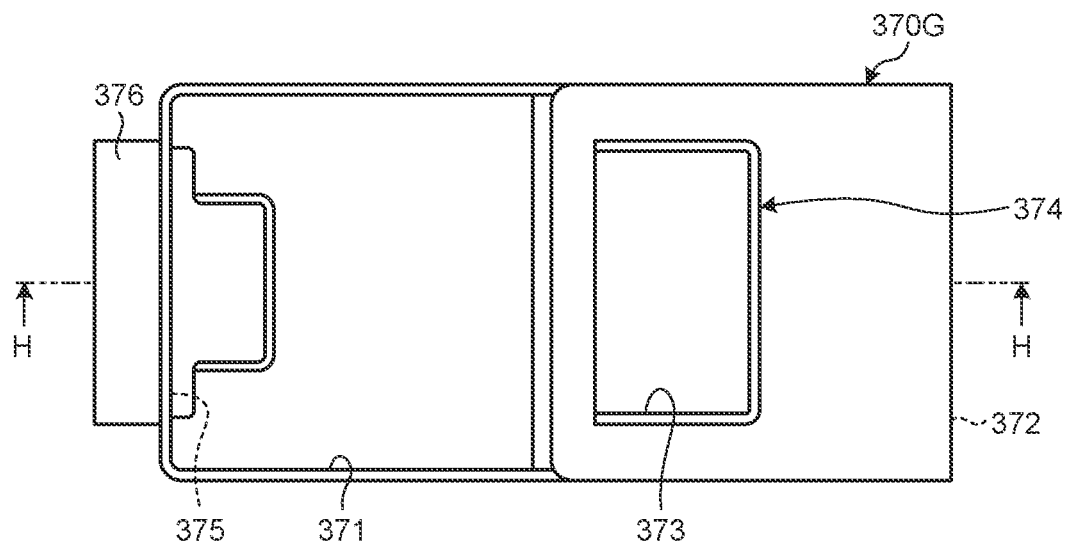
FIG. 28 is a plan view illustrating the configuration of the duct provided in the processing device included in the endoscope system according to the modified example of the second embodiment of the disclosure.
Figure 29:
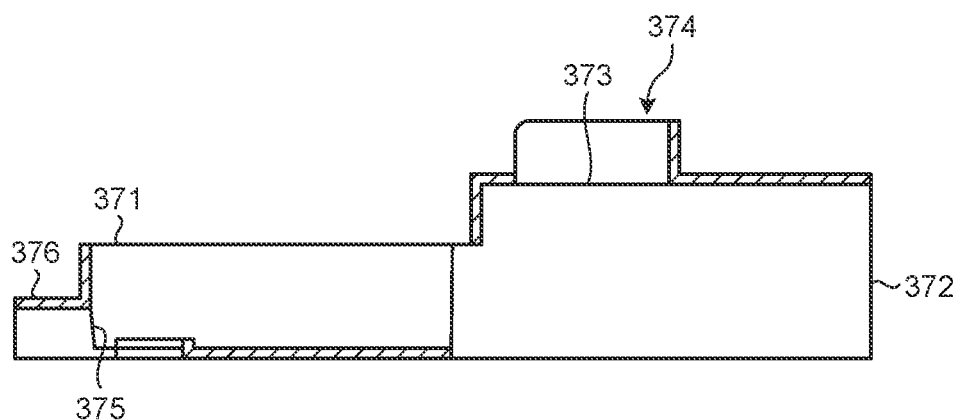
FIG. 29 is a partial sectional view of the duct corresponding to a cross section cut by a line H-H illustrated in FIG. 28.

A modified example of the second embodiment of the disclosure will be described next by reference to FIG. 27 to FIG. 29. FIG. 27 is a perspective view illustrating a configuration of a duct provided in a processing device included in an endoscope system according to the modified example of the second embodiment of the disclosure. FIG. 28 is a plan view illustrating the configuration of the duct provided in the processing device included in the endoscope system according to the modified example of the second embodiment of the disclosure. FIG. 29 is a sectional view taken upon a line H-H illustrated in FIG. 28. The endoscope system according to this modified example has the same configuration as that of the second embodiment described above, except that the endoscope system according to this modified example has a duct 370G instead of the duct 370F of the second embodiment. The duct 370G having a configuration different from that of the second embodiment will thus be described hereinafter.

A first opening 371, a second opening 372, a third opening 373, and a fourth opening 375 are formed in the duct 370G, similarly to the duct 370F. A wall 374 is provided in a standing manner on an outer edge of the third opening 373 of the duct 370G.

A protruding portion 376 is provided in a standing manner on an outer edge of the fourth opening 375 of the duct 370G. The protruding portion 376 extends, from the outer edge of the fourth opening 375, perpendicularly to a surface where the fourth opening 375 is formed. The protruding portion 376 surrounds at least part of the fourth opening 375. The protruding portion 376 illustrated in FIG. 27 to FIG. 29 extends from a portion of the rectangular outer edge forming an opening of the fourth opening 375, the portion corresponding to three sides of the rectangular outer edge.

In a case where the first fan 330 and the second fan 340 are being driven, the airflow F1 is generated in the housing 30 (see FIG. 9).

However, when the first fan 330 stops being driven, the flow of air entering the duct 370G from the first opening 371 becomes stagnant. When this happens, the airflow F2 (see FIG. 9) is generated in the duct 370G. In this airflow F2, air enters the duct 370E from the third opening 373 and is released from the second opening 372. The air in the airflow F2 collides with the wall 374 after entering the housing 30, flows toward the third opening 373, and enters the duct 370G. Intake of air by means of the wall 374 enables air to be sent into the duct 370G. This generation of the airflow F2 enables the flow of air via the heatsink 360 to be maintained even in a case where the first fan 330 stops being driven.

Air is also taken into the duct 370E from the fourth opening 375. Therefore, as compared to the case where air is taken in from the third opening 373 only, the amount of air that is able to be taken into the duct 370G is increased and the amount of passed through the heatsink 360 is thus able to be increased. What is more, external air is able to be taken into the duct 370G even more efficiently because the protruding portion 376 enables all of the air passing near the fourth opening 375 to be taken into the duct 370G.

In the above described modified example, a configuration that releases the heat taken into the heatsink 360 to the exterior of the housing includes the third opening 373 and the wall 374 that are formed in the duct 370G, through which air is sent to the heatsink 360. The third opening 373 is different from the first opening 371 where the first fan 330 is arranged, and the wall 374 is provided to stand externally from the third opening 373 to send air into the duct 370G. The modified example enables efficient ventilation in the housing because air colliding with the wall 374 is taken into the duct 370G via the third opening 373 and passage of the air to the heatsink 360 is thus able to be maintained even in a case where the fan stops being driven.

The modified example also enables increase in the amount of air passing through the duct 370E and even more efficient cooling of the heatsink 360 because the fourth opening 375 is formed in the duct 370G. The protruding portion 376 surrounding part of the fourth opening 375 is provided, and air is thus able to be taken into the duct 370E additionally from this fourth opening 375.

Third Embodiment

Figure 30:
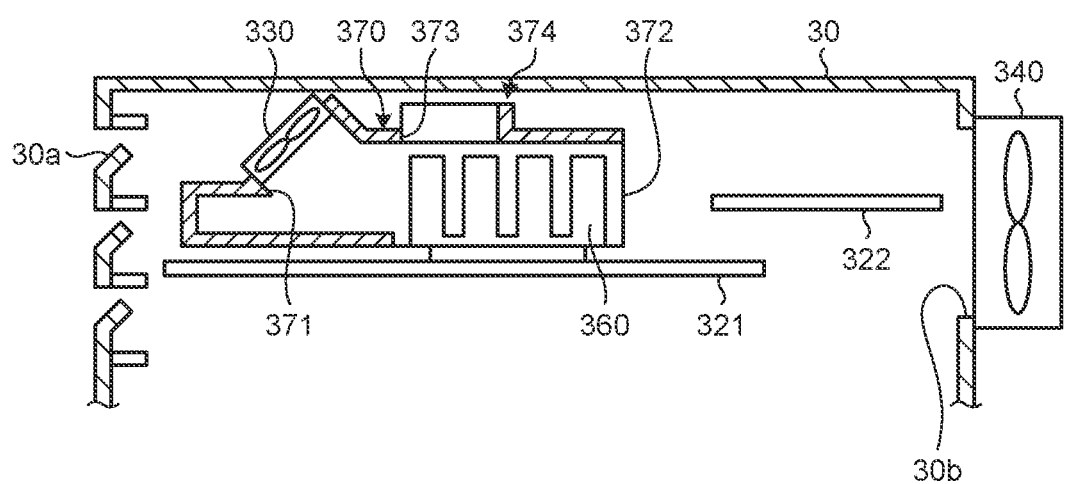
FIG. 30 is a diagram illustrating a configuration of a cooling unit provided in a processing device included in an endoscope system according to a third embodiment of the disclosure.

A third embodiment of the disclosure will be described next by reference to FIG. 30. FIG. 30 is a diagram illustrating a configuration of a cooling unit provided in a processing device included in an endoscope system according to the third embodiment of the disclosure. The endoscope system according to the third embodiment has the same configuration as the endoscope system 1 described above, except that the installation angle of the first fan 330 in the endoscope system 1 has been changed in the endoscope system according to the third embodiment.

In this third embodiment, a first fan 330 is arranged such that the blowing direction (the installation direction of the blades) of the first fan 330 is inclined at 45° with respect to the blowing direction (the installation direction of the blades) of the second fan 340. As long as air is able to be taken into the duct 370, without being limited to 45°, this angle of inclination may be set at an angle other than 90° (a right angle).

The above described third embodiment also has effects similar to those of the first embodiment. In addition, the efficiency of the intake of air into the duct 370 is able to be improved by the adjustment of the blowing direction of the first fan 330.

Fourth Embodiment

Figure 31:
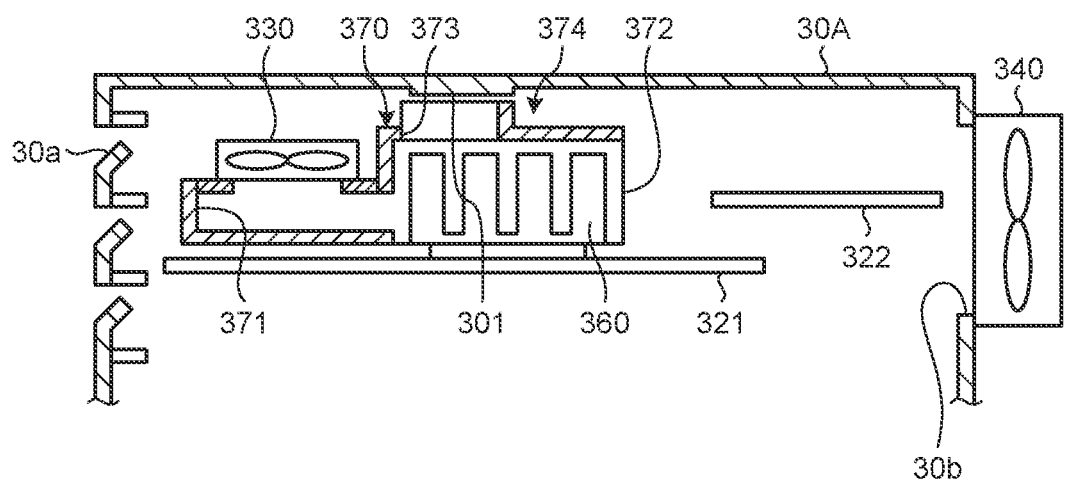
FIG. 31 is a diagram illustrating a configuration of a cooling unit provided in a processing device included in an endoscope system according to a fourth embodiment of the disclosure.

A fourth embodiment of the disclosure will be described next by reference to FIG. 31. FIG. 31 is a diagram illustrating a configuration of a cooling unit provided in a processing device included in an endoscope system according to the fourth embodiment of the disclosure. The endoscope system according to the fourth embodiment has the same configuration as the endoscope system 1 described above, except that the configuration of the housing 30 in the endoscope system 1 has been changed in the endoscope system according to the fourth embodiment.

A housing 30A according to this fourth embodiment has a stepped portion 301 that is formed on a wall surface (an inner wall) facing the third opening 373 of the duct 370 and that protrudes to the interior of the housing 30A. Forming this stepped portion 301 reduces the distance between the wall 374 and the inner wall of the housing 30A and thus enables reduction in the amount of air passing between the wall 374 and the inner wall of the housing 30A. As a result, the amount of air taken in from the third opening 373 is able to be increased.

The above described fourth embodiment also has effects similar to those of the first embodiment. In addition, adjusting the amount of protrusion of the stepped portion 301 enables adjustment of the efficiency of the intake of air into the duct 370.

Fifth Embodiment

Figure 32:
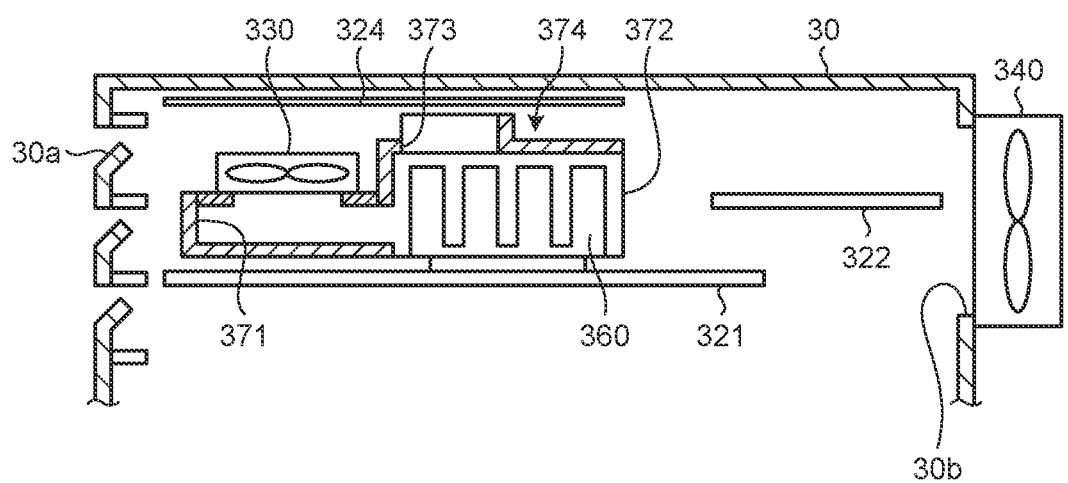
FIG. 32 is a diagram illustrating a configuration of a cooling unit provided in a processing device included in an endoscope system according to a fifth embodiment of the disclosure.

A fifth embodiment of the disclosure will be described next by reference to FIG. 32. FIG. 32 is a diagram illustrating a configuration of a cooling unit provided in a processing device included in an endoscope system according to the fifth embodiment of the disclosure.

In this fifth embodiment, a member 324 that is plate-shaped is installed between an inner wall of the housing 30 and the duct 370. The member 324 has a plane facing the surface of the duct 370, the surface being where the third opening 373 is formed. Installing this member 324 makes the distance between the wall 374 and the member 324 shorter than the distance between the inner wall of the housing 30 and the duct 370 and thus enables the amount of air taken into the duct 370 from the third opening 373 to be increased.

The above described fifth embodiment also has effects similar to those of the first embodiment. In addition, adjusting the position and/or angle of the member 324 enables adjustment of the efficiency of the intake of air into the duct 370.

The example where the illumination unit 3a is integrated with the processing device 3 has been described above with respect to the first to fifth embodiments, but the illumination unit 3a and the processing device 3 may be separately bodied and the light source unit 300, the light source driver 310, and the illumination control unit 320 may be provided outside the processing device 3, for example. In that case, the cooling unit 3c may be provided in each unit having any heat generating element.

Furthermore, the example where the first opening 371, the second opening 372, and the third opening 373 each have an outer edge forming a rectangular or trapezoidal opening has been described above with respect to the first to fifth embodiments, but they may each be configured to have an outer edge forming an oval or circular opening, for example.

Furthermore, according to the above description of the first to fifth embodiments, the endoscope system according to the disclosure is related to the endoscope system 1 where the flexible endoscope 2 for observation of body tissue inside subjects is used, but the endoscope system is also applicable to an endoscope system where a rigid endoscope, an industrial endoscope for observation of characteristics of materials, a fiberscope, or a device having a camera head connected to an eyepiece unit of an optical endoscope, such as an optical telescope, is used.

As described above, a cooling device of an endoscope according to the disclosure is useful for efficient ventilation in a housing even in a case where a fan stops being driven.

The disclosure has an effect of enabling efficient ventilation in a housing even in a case where a fan has stopped being driven.

Additional advantages and modifications will readily occur to those skilled in the art. Therefore, the disclosure in its broader aspects not limited to the specific details and representative embodiments shown and described herein. Accordingly, various modifications may be made without departing from the spirit or scope of the general inventive concept as defined by the appended claims and their equivalents.

What is claimed is:

1. A cooling device of an endoscope device, the cooling device comprising:
    a box;
    a first communicating hole that is a hole provided in the box;
    a second communicating hole that is a hole provided in the box;
    a second fan that is provided at the second communicating hole, the second fan being configured to guide gas to an exterior of the box through the second communicating hole to generate an airflow in the box, the gas having introduced into the box from the first communicating hole; and
    a duct configured to house a heat generator to be cooled, the duct being positioned is the box to allow the airflow to pass through an inside of the duct,
    the duct comprising
        a first opening positioned upstream of the heat generator,
        a first fan that is provided at the first opening, the first fan being configured to guide the airflow into the duct to cause the airflow to come into contact with the heat generator,
        a second opening that is positioned downstream from the heat generator, the second opening being configured to guide the airflow taken in by the first fan to an exterior of the duct,
        a third opening that is provided downstream from the first opening and upstream of the second opening and that is open on a surface that is along a surface where the first opening is open, and
        a wall that includes as elevated portion on a periphery of the third opening to adjust the airflow, the elevated portion making a downstream side of the periphery higher than as upstream side of the periphery to allow the gas to flow into the duct from the third opening upon stoppage of the first fan.

2. The cooling device according to claim 1, wherein the third opening is arranged side by side with the first opening and stepped up from the first opening.

3. The cooling device according to claim 1, wherein
    the heat generator comprises a heat generating element and a heatsink in contact with the heat generating element, and
    the duct is configured such that the gas passes through the heatsink in both a case where the gas flows into the duct from the first opening and a case where the gas flows into the duct from the third opening.

4. The cooling device according to claim 1, wherein the duct further comprises a fourth opening provided upstream of the first fan along the airflow.

5. The cooling device according to claim 1, further comprising a controller configured to
    determine whether or not the first fan is stopped when controlling driving of the first and second fans; and
    increase output of the second fan when it is determined that the first fan is stopped.

6. The cooling device according to claim 5, wherein the controller is configured to
    determine whether or not the second fan is stopped when controlling the driving of the first and second fans; and
    increase output of the first fan when it is determined that the second fan is stopped.

7. The cooling device according to claim 1, further comprising a plate-shaped member that is separate from the third opening by a predetermined distance the member being configured to cover the third opening.

8. The cooling device according to claim 1, wherein
the third opening is arranged side by side with the first opening in the duct, and
the duct is arranged such that the third opening is nearer to an inner surface of the box than the first opening is.

9. The cooling device according to claim 1, wherein the first fan has a blade extending along the surface where the first opening is open.

10. An endoscope processing device, comprising:
the cooling device according to claim 1.

11. A cooling device of an endoscope device, the cooling device comprising:
a box;
a first communicating portion that is a hole provided in the box;
a second communicating portion that is a hole provided in the box;
a second fan that is provided at the second communicating portion, the second fan being configured to guide gas to as exterior of the box through the second communicating portion to generate an airflow in the box, the gas having introduced into the box from the first communicating portion; and
a duct configured to house a heat generator to be cooled, the duct being positioned in the box to allow the airflow to pass through an inside of the duct,
the duct comprising
a first opening positioned upstream of the heat generator,
a first fan that is provided at the first opening, the first fan being configured to guide the airflow into the duct to cause the airflow to come into contact with the heat generator,
a second opening that is positioned downstream from the heat generator, the second opening being configured to guide the airflow taken in by the first fan to an exterior of the duct,
a third opening that is provided downstream from the first opening and upstream of the second opening and that is open on a surface that is along a surface where the first opening is open, and
a wall that includes an elevated portion on a periphery of the third opening to adjust the airflow, the elevated portion making a downstream side of the periphery higher than an upstream side of the periphery to allow the gas to flow into the duct from the third opening upon stoppage of the first fan.

* * * * *